(12) United States Patent
Worrell et al.

(10) Patent No.: US 9,545,253 B2
(45) Date of Patent: Jan. 17, 2017

(54) SURGICAL INSTRUMENT WITH CONTAINED DUAL HELIX ACTUATOR ASSEMBLY

(71) Applicant: Ethicon Endo-Surgery, Inc., Cincinnati, OH (US)

(72) Inventors: Barry C. Worrell, Centerville, OH (US); Jason R. Lesko, Harrison, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 531 days.

(21) Appl. No.: 13/622,735

(22) Filed: Sep. 19, 2012

(65) Prior Publication Data
US 2013/0023868 A1      Jan. 24, 2013

Related U.S. Application Data

(63) Continuation-in-part of application No. 13/235,623, filed on Sep. 19, 2011.
(Continued)

(51) Int. Cl.
*A61B 17/29* (2006.01)
*A61B 17/072* (2006.01)
(Continued)

(52) U.S. Cl.
CPC ..... *A61B 17/07207* (2013.01); *A61B 18/1445* (2013.01); *A61B 18/1447* (2013.01);
(Continued)

(58) Field of Classification Search
CPC ............ A61B 18/1445; A61B 18/1442; A61B 2018/0063
(Continued)

(56) References Cited

U.S. PATENT DOCUMENTS 2,818,744 A    1/1958    Moody
2,857,776 A    10/1958   Williams
(Continued)

FOREIGN PATENT DOCUMENTS

CN    1163558 A     10/1997
DE    43 00 307     7/1994
(Continued)

OTHER PUBLICATIONS

Abstract and Machine Translation of German Patent No. DE 43 00 307.
(Continued)

*Primary Examiner* — Alyssa M Alter
(74) *Attorney, Agent, or Firm* — Frost Brown Todd LLC

(57) ABSTRACT

An apparatus comprises an end effector, an elongate shaft, and a handle assembly. The shaft includes an articulation section that is operable to deflect the end effector away from the longitudinal axis of the shaft. The handle assembly includes a rotary member positioned within an intermediate section of the handle assembly. The rotary member is rotatable about an axis that is parallel to the longitudinal axis of the shaft. The rotary member is operable to control the articulation section of the shaft. The rotary member may include opposing thread sections that simultaneously drive lead screws in opposite longitudinal directions, to thereby control the articulation section. The shaft may be rotatable relative to the handle assembly, and the apparatus may selectively lock or resist such rotation based on the articulation state of the articulation section.

20 Claims, 31 Drawing Sheets

Related U.S. Application Data

(60) Provisional application No. 61/386,094, filed on Sep. 24, 2010.

(51) Int. Cl.
*A61B 18/14* (2006.01)
*A61B 17/00* (2006.01)
*A61B 18/00* (2006.01)

(52) U.S. Cl.
CPC .............. *A61B 2017/0038* (2013.01); *A61B 2017/2908* (2013.01); *A61B 2017/2927* (2013.01); *A61B 2017/2946* (2013.01); *A61B 2018/00642* (2013.01); *A61B 2018/00702* (2013.01); *A61B 2018/00791* (2013.01); *A61B 2018/00815* (2013.01); *A61B 2018/00875* (2013.01); *A61B 2018/00892* (2013.01); *A61B 2018/1452* (2013.01); *A61B 2018/1455* (2013.01)

(58) Field of Classification Search
USPC ............................................ 606/51, 33, 130
See application file for complete search history.

(56) References Cited

U.S. PATENT DOCUMENTS

| | | |
|---|---|---|
| 2,881,645 A | 4/1959 | Kruchten |
| 3,194,530 A | 7/1965 | Heyl |
| 2,715,341 A | 8/1965 | Hogan |
| 4,203,430 A | 5/1980 | Takahashi |
| 4,483,562 A | 11/1984 | Schoolman |
| 4,723,936 A | 2/1988 | Buchbinder et al. |
| 4,880,015 A | 11/1989 | Nierman |
| 4,945,920 A | 8/1990 | Clossick |
| 5,020,514 A | 6/1991 | Heckele |
| 5,125,895 A | 6/1992 | Buchbinder et al. |
| 5,171,249 A | 12/1992 | Stefanchik et al. |
| 5,330,502 A | 7/1994 | Hassler et al. |
| 5,383,888 A | 1/1995 | Zvenyatsky et al. |
| 5,391,180 A | 2/1995 | Tovey et al. |
| 5,395,329 A | 3/1995 | Fleischhacker et al. |
| 5,409,498 A | 4/1995 | Braddock et al. |
| 5,411,519 A | 5/1995 | Tovey et al. |
| 5,441,499 A | 8/1995 | Fritzsch |
| 5,454,827 A | 10/1995 | Aust et al. |
| 5,462,546 A | 10/1995 | Rydell |
| 5,514,130 A | 5/1996 | Baker |
| 5,514,157 A | 5/1996 | Nicholas et al. |
| 5,540,685 A | 7/1996 | Parins et al. |
| 5,549,637 A | 8/1996 | Crainich |
| 5,562,682 A | 10/1996 | Oberlin et al. |
| 5,582,617 A | 12/1996 | Klieman et al. |
| 5,607,450 A | 3/1997 | Zvenyatsky et al. |
| 5,609,601 A | 3/1997 | Kolesa et al. |
| 5,626,587 A | 5/1997 | Bishop et al. |
| 5,632,432 A | 5/1997 | Schulze et al. |
| 5,643,294 A | 7/1997 | Tovey et al. |
| 5,673,841 A | 10/1997 | Schulze et al. |
| 5,700,275 A | 12/1997 | Bell et al. |
| 5,704,534 A | 1/1998 | Huitema et al. |
| 5,743,456 A | 4/1998 | Jones et al. |
| 5,766,196 A | 6/1998 | Griffiths |
| 5,766,205 A | 6/1998 | Zvenyatsky et al. |
| 5,782,859 A | 7/1998 | Nicholas et al. |
| 5,817,119 A | 10/1998 | Klieman et al. |
| 5,833,695 A | 11/1998 | Yoon |
| 5,921,956 A | 7/1999 | Grinberg et al. |
| 5,931,832 A | 8/1999 | Jensen |
| 6,010,054 A | 1/2000 | Johnson et al. |
| 6,162,208 A | 12/2000 | Hipps |
| 6,179,809 B1 | 1/2001 | Khairkhahan et al. |
| 6,423,059 B1 | 7/2002 | Hanson et al. |
| 6,500,176 B1 | 12/2002 | Truckai et al. |
| 6,554,794 B1 | 4/2003 | Mueller et al. |
| RE38,335 E | 11/2003 | Aust et al. |
| 6,783,524 B2 | 8/2004 | Anderson et al. |
| 6,978,921 B2 | 12/2005 | Shelton et al. |
| 6,991,627 B2 | 1/2006 | Madhani et al. |
| 7,004,938 B2 | 2/2006 | Ormsby et al. |
| 7,055,731 B2 | 6/2006 | Shelton et al. |
| 7,070,595 B2 | 7/2006 | Ormsby et al. |
| 7,081,114 B2 | 7/2006 | Rashidi |
| 7,087,071 B2 | 8/2006 | Nicholas et al. |
| 7,112,201 B2 | 9/2006 | Truckai et al. |
| 7,125,409 B2 | 10/2006 | Truckai et al. |
| 7,128,254 B2 | 10/2006 | Shelton et al. |
| 7,141,897 B2 | 11/2006 | Park |
| 7,143,925 B2 | 12/2006 | Shelton et al. |
| 7,150,749 B2 | 12/2006 | Dycus et al. |
| 7,156,846 B2 | 1/2007 | Dycus et al. |
| 7,159,750 B2 | 1/2007 | Racenet et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,208,005 B2 | 4/2007 | Frecker et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,380,696 B2 | 6/2008 | Shelton, IV et al. |
| 7,381,209 B2 | 6/2008 | Truckai et al. |
| 7,404,508 B2 | 7/2008 | Smith et al. |
| 7,407,076 B2 | 8/2008 | Racenet et al. |
| 7,424,965 B2 | 9/2008 | Racenet et al. |
| 7,455,208 B2 | 11/2008 | Wales et al. |
| 7,464,849 B2 | 12/2008 | Shelton, IV et al. |
| 7,481,348 B2 | 1/2009 | Marczyk |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,540,872 B2 * | 6/2009 | Schechter et al. ............... 606/50 |
| 7,549,564 B2 | 6/2009 | Boudreaux |
| 7,553,275 B2 | 6/2009 | Padget et al. |
| 7,559,450 B2 | 7/2009 | Wales et al. |
| 7,584,880 B2 | 9/2009 | Racenet et al. |
| 7,594,913 B2 | 9/2009 | Ormsby et al. |
| 7,597,230 B2 | 10/2009 | Racenet et al. |
| 7,615,044 B2 | 11/2009 | Scheibe et al. |
| 7,654,431 B2 | 2/2010 | Hueil et al. |
| 7,691,095 B2 | 4/2010 | Bednarek et al. |
| 7,703,653 B2 | 4/2010 | Shah et al. |
| 7,708,182 B2 | 5/2010 | Viola |
| 7,721,935 B2 | 5/2010 | Racenet et al. |
| 7,766,910 B2 | 8/2010 | Hixson et al. |
| 7,771,425 B2 | 8/2010 | Dycus et al. |
| 7,780,054 B2 | 8/2010 | Wales |
| 7,784,662 B2 | 8/2010 | Wales et al. |
| 7,793,814 B2 | 9/2010 | Racenet et al. |
| 7,798,386 B2 | 9/2010 | Schall et al. |
| 7,799,028 B2 | 9/2010 | Schechter et al. |
| 7,815,090 B2 | 10/2010 | Marczyk |
| 7,815,091 B2 | 10/2010 | Marczyk |
| 7,815,637 B2 | 10/2010 | Ormsby et al. |
| 7,819,298 B2 | 10/2010 | Hall et al. |
| 7,828,725 B2 | 11/2010 | Maruyama |
| 7,832,408 B2 | 11/2010 | Shelton et al. |
| 7,842,025 B2 | 11/2010 | Coleman et al. |
| 7,909,220 B2 | 3/2011 | Viola |
| 8,006,365 B2 | 8/2011 | Levin et al. |
| 8,033,441 B2 | 10/2011 | Marczyk |
| 8,062,306 B2 | 11/2011 | Nobis et al. |
| 8,092,451 B2 | 1/2012 | Schechter et al. |
| 8,100,309 B2 | 1/2012 | Marczyk |
| 8,142,473 B2 | 3/2012 | Cunningham |
| 8,152,799 B2 | 4/2012 | Ormsby et al. |
| 8,161,838 B2 | 4/2012 | Duval |
| 8,197,479 B2 | 6/2012 | Olson et al. |
| 8,205,619 B2 | 6/2012 | Shah et al. |
| 8,236,010 B2 | 8/2012 | Ortiz et al. |
| 8,241,320 B2 | 8/2012 | Lyons et al. |
| 8,292,147 B2 | 10/2012 | Viola |

(56) References Cited

U.S. PATENT DOCUMENTS

| | | |
|---|---|---|
| 8,292,889 B2 | 10/2012 | Cunningham et al. |
| 8,308,659 B2 | 11/2012 | Scheibe et al. |
| 8,317,811 B2 | 11/2012 | Laporte Rosello et al. |
| 8,323,239 B2 | 12/2012 | Bednarek et al. |
| 8,323,297 B2 | 12/2012 | Hinman et al. |
| 8,353,902 B2 | 1/2013 | Prakash |
| 8,357,161 B2 | 1/2013 | Mueller |
| 8,361,067 B2 | 1/2013 | Pellegrino et al. |
| 8,366,709 B2 | 2/2013 | Schechter et al. |
| 8,372,064 B2 | 2/2013 | Douglass et al. |
| 8,398,673 B2 | 3/2013 | Hinchliffe et al. |
| 8,403,832 B2 | 3/2013 | Cunningham et al. |
| 8,403,945 B2 | 3/2013 | Whitfield et al. |
| 8,789,741 B2 | 7/2014 | Baxter, III et al. |
| 9,089,327 B2 | 7/2015 | Worrell et al. |
| 2003/0163085 A1 | 8/2003 | Tanner et al. |
| 2006/0259071 A1 | 11/2006 | Nicholas et al. |
| 2007/0043353 A1 | 2/2007 | Dycus et al. |
| 2007/0219550 A1 | 9/2007 | Thompson et al. |
| 2007/0282324 A1 | 12/2007 | Vaska et al. |
| 2008/0161798 A1 | 7/2008 | Podmore et al. |
| 2009/0088792 A1 | 4/2009 | Hoell et al. |
| 2009/0125019 A1 | 5/2009 | Douglass et al. |
| 2009/0198272 A1 | 8/2009 | Kerver et al. |
| 2009/0283568 A1 | 11/2009 | Racenet et al. |
| 2010/0094289 A1 | 4/2010 | Taylor et al. |
| 2010/0179540 A1 | 7/2010 | Marczyk et al. |
| 2010/0179545 A1 | 7/2010 | Twomey et al. |
| 2010/0193566 A1 | 8/2010 | Scheib et al. |
| 2010/0249759 A1 | 9/2010 | Hinman et al. |
| 2010/0298824 A1 | 11/2010 | Rothstein et al. |
| 2011/0009863 A1 | 1/2011 | Marczyk et al. |
| 2011/0087218 A1 | 4/2011 | Boudreaux et al. |
| 2011/0184459 A1 | 7/2011 | Malkowski et al. |
| 2011/0213360 A1 | 9/2011 | Cunningham et al. |
| 2011/0213361 A1 | 9/2011 | Cunningham et al. |
| 2011/0213363 A1 | 9/2011 | Cunningham et al. |
| 2011/0230875 A1 | 9/2011 | Walberg et al. |
| 2011/0264074 A1 | 10/2011 | Tegg et al. |
| 2011/0282176 A1 | 11/2011 | Tegg |
| 2012/0074200 A1 | 3/2012 | Schmid et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078248 A1 | 3/2012 | Worrell et al. |
| 2012/0109186 A1 | 5/2012 | Parrott et al. |
| 2012/0116379 A1 | 5/2012 | Yates et al. |
| 2012/0143088 A1 | 6/2012 | Schultz |
| 2012/0179151 A1 | 7/2012 | Mueller |
| 2012/0203169 A1 | 8/2012 | Tegg |
| 2012/0215220 A1 | 8/2012 | Kerver et al. |
| 2012/0253326 A1 | 10/2012 | Kleyman |
| 2012/0265186 A1 | 10/2012 | Burger et al. |
| 2012/0303013 A1 | 11/2012 | Burell et al. |
| 2012/0316560 A1 | 12/2012 | Hassoun |
| 2013/0012929 A1 | 1/2013 | Malkowski |
| 2013/0012986 A1 | 1/2013 | Suzuki |
| 2013/0026868 A1 | 1/2013 | Klafter et al. |
| 2013/0032627 A1 | 2/2013 | Viola |
| 2013/0041403 A1 | 2/2013 | Cunningham et al. |
| 2013/0096407 A1 | 4/2013 | Bednarek et al. |

FOREIGN PATENT DOCUMENTS

| | | |
|---|---|---|
| EP | 1637086 | 3/2006 |
| EP | 2151204 | 2/2010 |
| EP | 2 198 787 | 6/2010 |
| FR | 2 915 873 | 11/2008 |
| WO | WO 00/67834 | 11/2000 |
| WO | WO 2008/045348 | 4/2008 |
| WO | WO 2010/104755 | 9/2010 |
| WO | WO 2011/044343 | 4/2011 |
| WO | WO 2012/067468 | 5/2012 |
| WO | WO 2012/078951 | 6/2012 |

OTHER PUBLICATIONS

Abstract and Machine Translation of French Patent No. FR 2 915 873.
International Search Report dated Jan. 30, 2014 for Application No. PCT/US2013/060537.
International Search Report dated Jan. 31, 2014 for Application No. PCT/US2013/060536.
International Search Report dated Jun. 13, 2012 for Application No. PCT/US2011/053016.
U.S. Appl. No. 13/622,729, filed Sep. 19, 2012, Worrell et al.
International Search Report dated Dec. 16, 2011 for Application No. PCT/US2011/052707.
International Search Report dated Dec. 28, 2011 for Application No. PCT/US2011/052712.
International Search Report and Written Opinion dated Jan. 24, 2012 for Application No. PCT/US2011/052734.
International Search Report dated Mar. 19, 2012 for Application No. PCT/US2011/053028.
Office Action Non-Final for dated Aug. 15, 2014 for U.S. Appl. No. 13/235,623.
Restriction Requirement dated Sep. 4, 2014 for U.S. Appl. No. 13/235,648.
Office Action Non-Final for dated Sep. 5, 2014 for U.S. Appl. No. 13/622,729.
U.S. Appl. No. 61/410,603, filed Nov. 5, 2010.
Australian Examiner's Report dated Aug. 15, 2013 for Application No. AU 2011305198, 5 pages.
Australian Examiner's Report dated Aug. 14, 2013 for Application No. AU 2011305205, 4 pages.
Australian Examiner's Report dated Aug. 8, 2013 for Application No. AU 2011305397, 5 pages.
Chinese First Office Action dated Dec. 17, 2014 for Application No. CN 2011800460673, 13 pages.
International Written Opinion dated Dec. 16, 2011 for Application No. PCT/US2011/052707, 7 pages.
International Written Opinion dated Dec. 28, 2011 for Application No. PCT/US2011/052712, 8 pages.
International Written Opinion dated Jun. 13, 2012 for Application No. PCT/US2011/053016, 8 pages.
International Written Opinion dated Mar. 19, 2012 for Application No. PCT/US2011/053028, 7 pages.
International Written Opinion dated Jan. 31, 2014 for Application No. PCT/US2013/060536, 5 pages.
International Written Opinion dated Jan. 30, 2014 for Application No. PCT/US2013/060537, 5 pages.
US Office Action, Final, dated Feb. 27, 2015 for U.S. Appl. No. 13/235,623, 11 pages.
US Office Action, Non-Final, dated Mar. 5, 2015 for U.S. Appl. No. 13/235,648, 11 pages.
US Office Action, Notice of Allowance, dated Dec. 17, 2014 for U.S. Appl. No. 13/622,729, 5 pages.
US Office Action, Notice of Allowance, dated Mar. 2, 2015 for U.S. Appl. No. 13/622,729, 5 pages.
Australian Examiner's Report dated May 28, 2015 for Application No. AU 2011305395, 4 pages.
Chinese First Office Action dated Dec. 8, 2014 for Application No. CN 2011800460565, 9 pages.
Chinese Second Office Action dated Sep. 1, 2015 for Application No. CN 2011800460565, 16 pages.
Chinese First Office Action dated Dec. 29, 2014 for Application No. CN 2011800460599, 15 pages.
Chinese Second Office Action dated Sep. 8, 2015 for Application No. CN 2011800460599, 5 pages.
Chinese First Office Action dated Feb. 4, 2015 for Application No. CN 2011800460654, 11 pages.
Chinese Second Office Action dated Oct. 10, 2015 for Application No. CN 2011800460654, 6 pages.
Japanese Office Action, Notification of Reasons for Refusal, dated Jun. 23, 2015 for Application No. JP 2013-530302, 4 pages.
Japanese Office Action, Notification of Reasons for Refusal, dated Jun. 9, 2015 for Application No. JP 2013-530303, 5 pages.

(56) References Cited

OTHER PUBLICATIONS

Japanese Office Action, Notification of Reasons for Refusal, dated Jun. 23, 2015 for Application No. JP 2013-530363, 4 pages.
Japanese Office Action, Notification of Reasons for Refusal, dated Jun. 23, 2015 for Application No. JP 2013-530365, 4 pages.
US Office Action, Final, dated Oct. 1, 2015 for U.S. Appl. No. 13/235,648, 14 pages.
U.S. Appl. No. 13/235,623.
U.S. Appl. No. 13/235,648.
U.S. Appl. No. 13/241,629.
Chinese Third Office Action dated Mar. 22, 2016 for Application No. CN 2011800460499, 5 pages.
Russian Office Action dated Jul. 1, 2015 for Application No. 2013118706, 5 pages.
US Office Action, Non-Final, dated Jun. 1, 2016 for U.S. Appl. No. 13/235,623, 10 pages.

\* cited by examiner

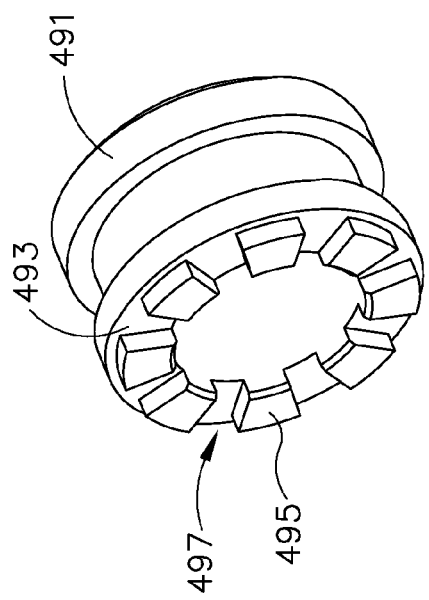
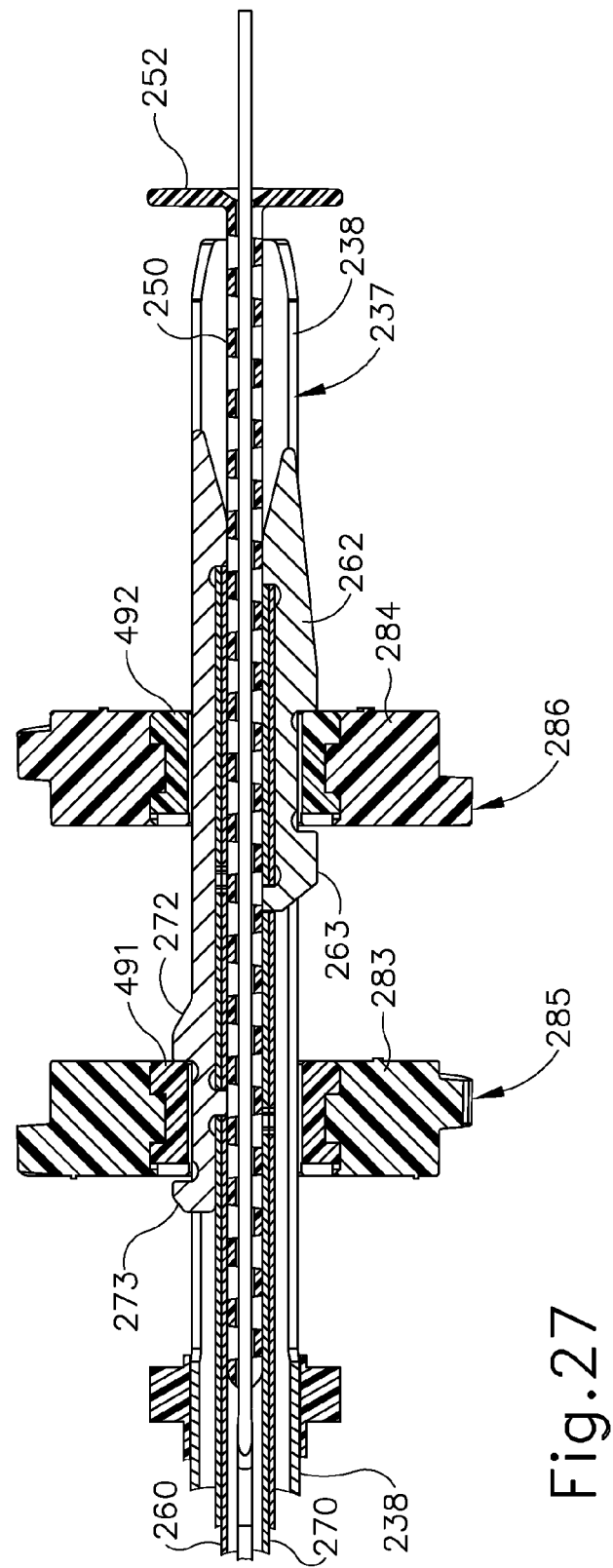

SURGICAL INSTRUMENT WITH CONTAINED DUAL HELIX ACTUATOR ASSEMBLY

PRIORITY

This application is a continuation-in-part of U.S. application Ser. No. 13/235,623, entitled "Control Features for Articulating Surgical Device," filed Sep. 19, 2011 and now published as U.S. Pub. No. 2012/0078243, the disclosure of which is incorporated by reference herein, and which claims priority to U.S. Provisional Application Ser. No. 61/386,094, filed Sep. 24, 2010, entitled "Articulating Surgical Device," the disclosure of which is incorporated by reference herein.

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 26 depicts a perspective view of an exemplary alternative rivet member that may be used in the articulation control components of a handle assembly;

FIG. 27 depicts a top cross-sectional view of articulation control components including the rivet member of FIG. 26;

Figure 1:
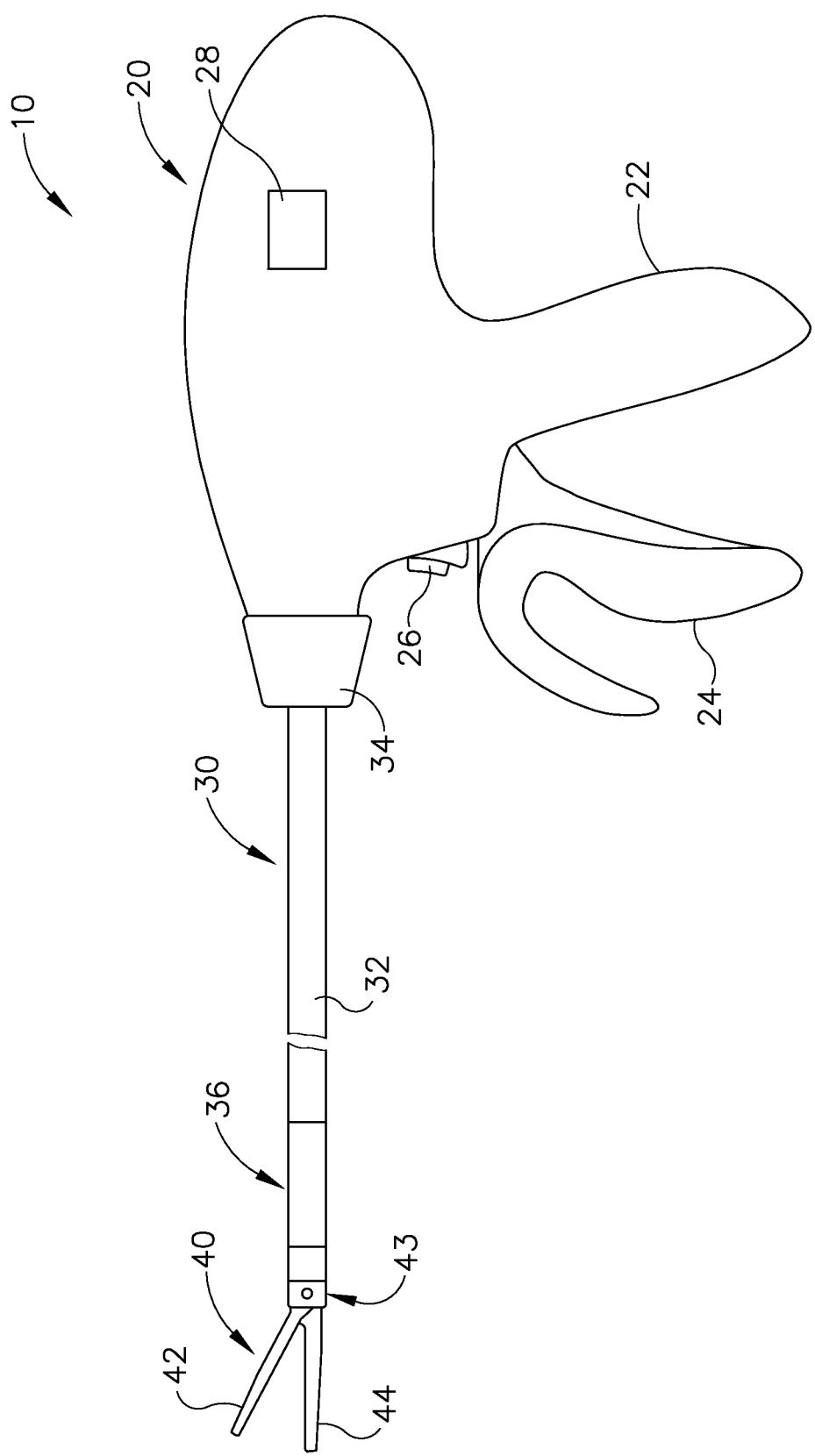
FIG. 1 depicts a side elevational view of an exemplary electrosurgical medical device.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; and/or U.S. Pub. No. 2012/0116379, now U.S. Pat. No. 9,161,803. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. It should be understood that pistol grip (22), trigger (24), and button (26) may be modified, substituted, supplemented, etc. in any suitable way, and that the descriptions of such components herein are merely illustrative. Articulation control (28) of the present example is operable to selectively control articulation section (36) of shaft (30), which will be described in greater detail below. Various examples of forms that articulation control (28) may take will also be described in greater detail below, while further examples will be apparent to those of ordinary skill in the art in view of the teachings herein.

Shaft (30) of the present example includes an outer sheath (32) and an articulation section (36). Articulation section (36) is operable to selectively position end effector (40) at various angles relative to the longitudinal axis defined by sheath (32). Various examples of forms that articulation section (36) and other components of shaft (30) may take will be described in greater detail below, while further examples will be apparent to those of ordinary skill in the art in view of the teachings herein. For instance, it should be understood that various components that are operable to actuate articulation section (36) may extend through the interior of sheath (32). In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

B. Exemplary End Effector

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 2:
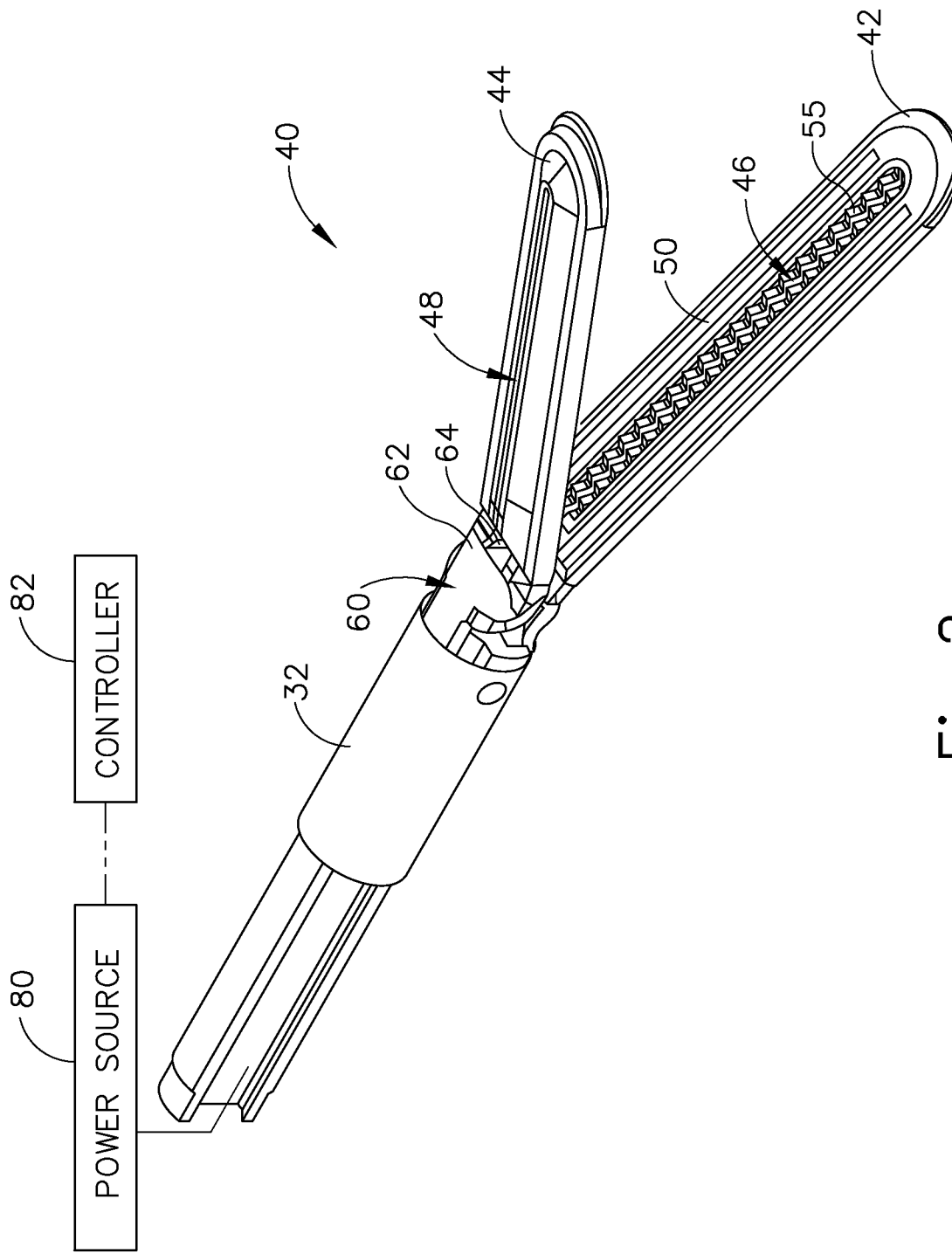
FIG. 2 depicts a perspective view of the end effector of the device of FIG. 1, in an open configuration.
Figure 3:
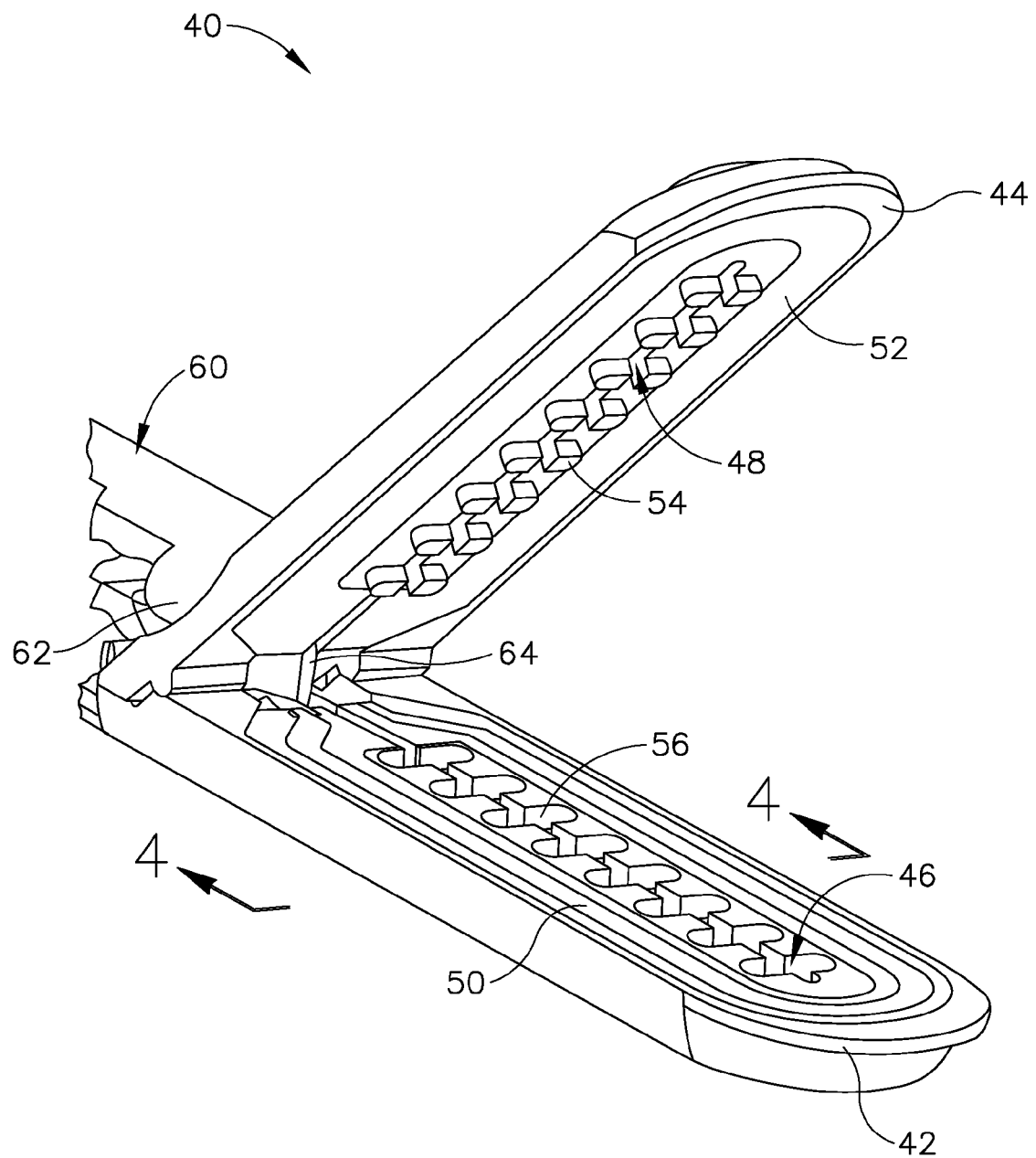
FIG. 3 depicts another perspective view of the end effector of the device of FIG. 1, in an open configuration.
Figure 4:
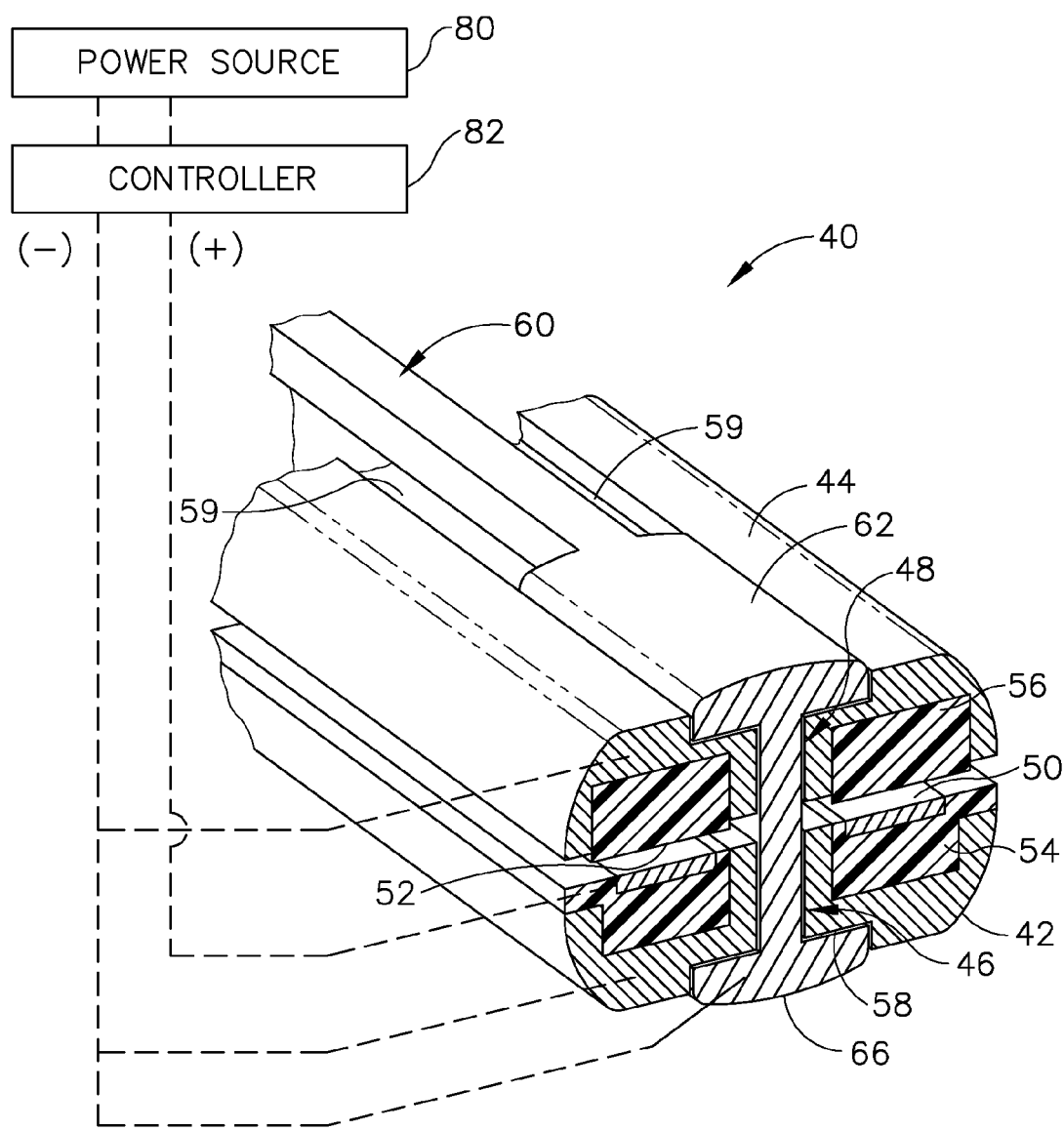
FIG. 4 depicts a cross-sectional end view of the end effector of FIG. 2, in a closed configuration and with the blade in a distal position, taken along line 4-4 of FIG. 3.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze grip (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (44) toward jaw (44) when firing beam (60) is actuated distally by squeezing trigger (24) toward pistol grip (22).

With tissue layers captured between jaws (42, 44) firing beam (60) continues to advance distally by the user squeezing trigger (24) toward pistol grip (22). As firing beam (60) advances distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52).

While several of the teachings below are described as variations to electrosurgical instrument (10), it should be understood that various teachings below may also be incorporated into various other types of devices. By way of example only, in addition to being readily incorporated into electrosurgical instrument (10), various teachings below may be readily incorporated into the devices taught in any of the references cited herein, other types of electrosurgical devices, surgical staplers, surgical clip appliers, and tissue graspers, among various other devices. Other suitable devices into which the following teachings may be incorporated will be apparent to those of ordinary skill in the art in view of the teachings herein.

II. Exemplary Articulation Joint Configurations

Articulation section (36) of shaft (30) may take a variety of forms. By way of example only, articulation section (36) may be configured in accordance with one or more teachings of U.S. Pub. No. 2012/0078247, entitled "Articulation Joint Features for Articulating Surgical Device," published Mar. 29, 2012, now U.S. Pat. No. 9,402,682, issued Aug. 2, 2016, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Furthermore, articulation section may be configured in accordance with the teachings of at least one other of the references cited herein. Various other suitable forms that articulation section (36) may take will be apparent to those of ordinary skill in the art in view of the teachings herein.

III. Exemplary Articulation Control Configurations

As noted above, some versions of handpiece (20) include an articulation control (28), which is operable to control articulation section (36) of shaft (30) to thereby selectively position end effector (40) at various angles relative to the longitudinal axis defined by sheath (32). Several examples of forms that articulation control (28) and other components of handpiece (20) may take will be described in greater detail below, while further examples will be apparent to those of ordinary skill in the art in view of the teachings herein. By way of example only, some merely illustrative alternative examples of articulation control (28) are disclosed in U.S. Pub. No. 2012/0078243, entitled "Control Features for Articulating Surgical Device," published Mar. 29, 2012, the disclosure of which is incorporated by reference herein; and in U.S. Pub. No. 2012/0078244, entitled "Control Features for Articulating Surgical Device," published Mar. 29, 2012, the disclosure of which is incorporated by reference herein.

A. Exemplary Articulation Control with Perpendicular Rotary Knob

Figure 5:
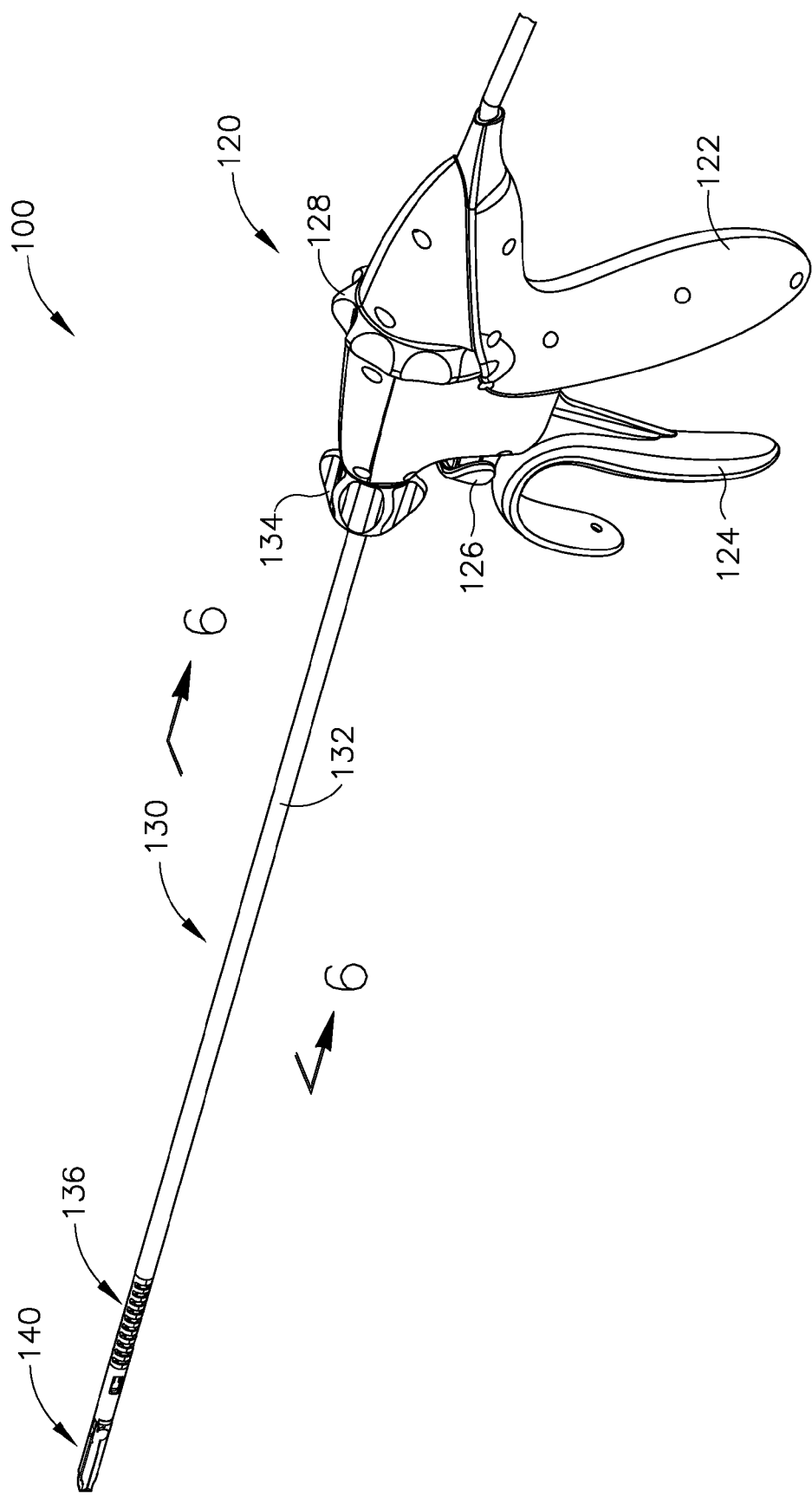
FIG. 5 depicts a perspective view of another exemplary electrosurgical medical device, with an articulation control knob.

FIG. 5 depicts an exemplary electrosurgical instrument (100) that includes a handpiece (120), a shaft (130) extending distally from handpiece (120), and an end effector (140) disposed at a distal end of shaft (130). Handpiece (120) of the present example includes a pistol grip (122), a pivoting trigger (124), an activation button (126), and a rotary articulation knob (128). Trigger (124) is pivotable toward and away from pistol grip (122) to selectively actuate end effector (140) as described above and as described in one or more of the references cited herein. Activation button (126) is operable to selectively activate RF circuitry that is in communication with end effector (140), as also described above and as described in one or more reference cited herein. In some versions, activation button (126) also serves as a mechanical lockout against trigger (124), such that trigger (124) cannot be fully actuated unless button (126) is being pressed simultaneously. Examples of how such a lockout may be provided are disclosed in one or more of the references cited herein. It should be understood that pistol grip (122), trigger (124), and button (126) may be modified, substituted, supplemented, etc. in any suitable way, and that the descriptions of such components herein are merely illustrative. Articulation knob (128) of the present example is operable to selectively control articulation section (136) of shaft (130), as will be described in greater detail below.

Shaft (130) of the present example includes an outer sheath (132), an articulation section (136) at the distal end of sheath (132), and a cutting member driver tube (138) that is slidably and coaxially disposed within sheath (132). Cutting member driver tube (138) is secured to a driver block (139), which is further secured to a cutting member (146) of end effector (140). Cutting member driver tube (138) is movable longitudinally to drive driver block (139) longitudinally, to thereby move cutting member (146) longitudinally. Cutting member (146) is essentially equivalent to firing beam (60) described above. The proximal portion (148) of end effector (140) includes an insert (not shown) that defines a channel containing the part of cutting member (146) that extends through proximal portion (148). This channel is configured to permit cutting member (146) to readily translate relative to the insert, while also preventing cutting member (146) from buckling within the insert when cutting member (146) encounters a load during distal advancement of cutting member (146).

Figure 13:
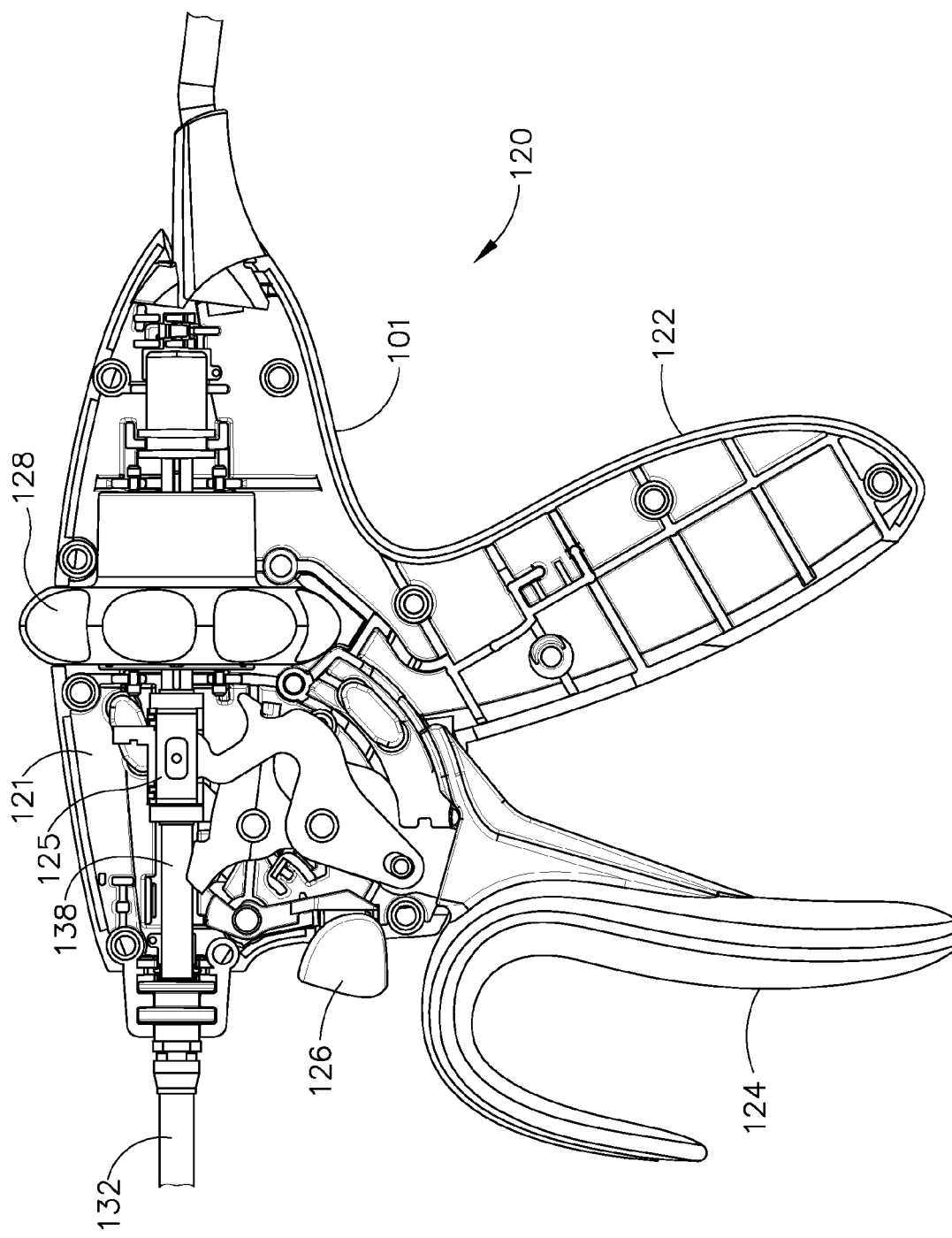
FIG. 13 depicts a side elevational view of the handle assembly of the device of FIG. 5, with a housing half removed.

In the present example, driver tube (138) is advanced distally by squeezing trigger (124) toward pistol grip (122); while driver tube (138) is retracted proximally by releasing trigger (124) and/or by actively moving trigger (124) away from pistol grip (122). As shown in FIG. 13, a yoke (125) couples trigger (124) with driver tube (138). Of course, cutting member (146) may be moved in any other suitable fashion. Articulation section (136) of the present example is operable to selectively position end effector (140) at various angles relative to the longitudinal axis defined by sheath (132). Various examples of forms that articulation section (136) and other components of shaft (130) may take are described in various references cited herein, while further examples will be apparent to those of ordinary skill in the art in view of the teachings herein. Similarly, end effector (140) may be configured in accordance with end effector (40) described above, in accordance with the teachings of various references cited herein, and/or in any other suitable way as will be apparent to those of ordinary skill in the art in view of the teachings herein.

In some versions, shaft (130) is also rotatable about the longitudinal axis defined by sheath (132), relative to handpiece (120), via a knob (134). Such rotation may provide rotation of end effector (140) and shaft (130) unitarily. In some other versions, knob (134) is operable to rotate end effector (140) without rotating any portion of shaft (130) that is proximal of articulation section (136). As another merely illustrative example, electrosurgical instrument (100) may include one rotation control that provides rotatability of shaft (130) and end effector (140) as a single unit; and another rotation control that provides rotatability of end effector (140) without rotating any portion of shaft (130) that is proximal of section (136). Other suitable rotation schemes will be apparent to those of ordinary skill in the art in view of the teachings herein. Of course, rotatable features may simply be omitted if desired.

Figure 6:
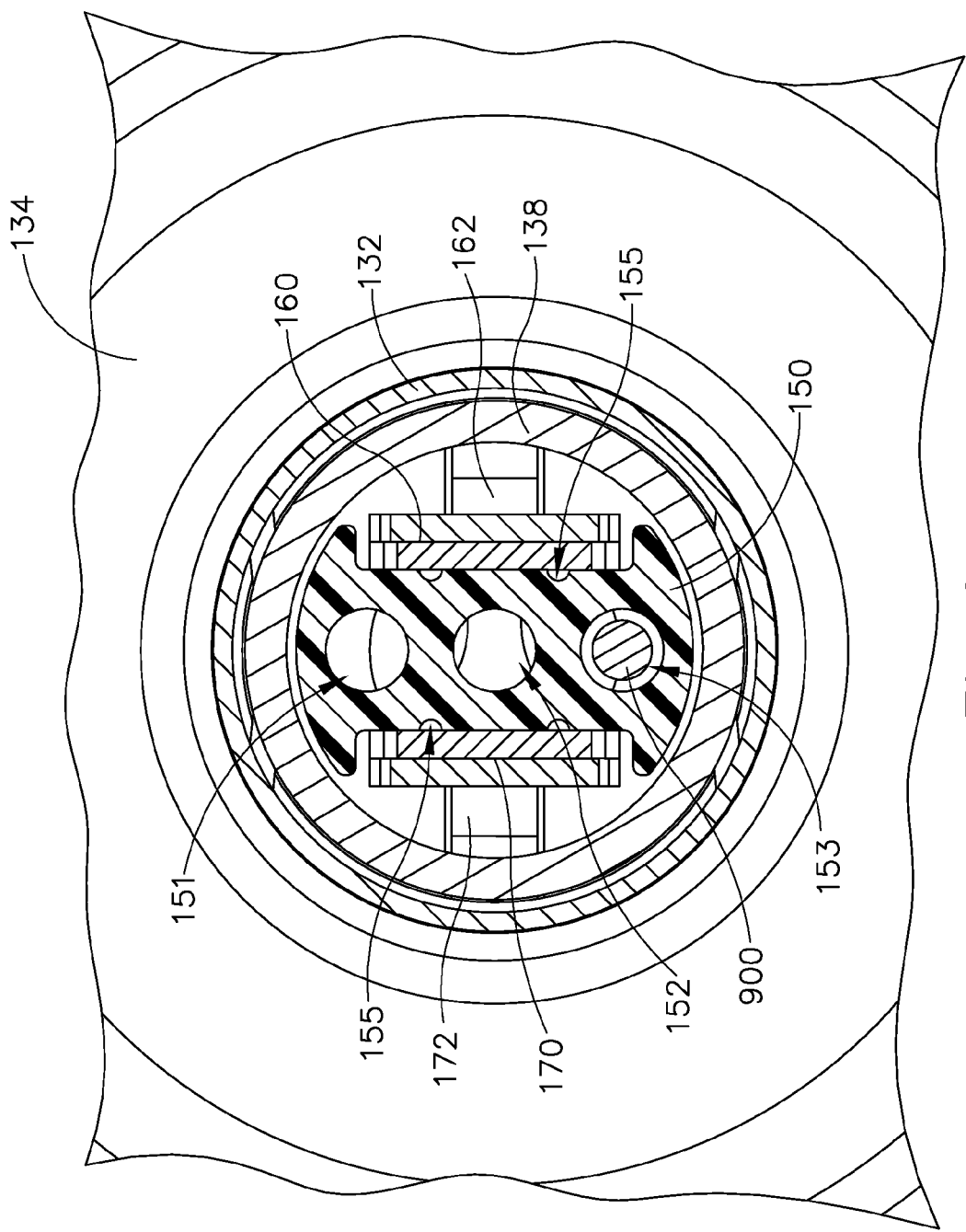
FIG. 6 depicts a cross-sectional end view of a shaft assembly of the device of FIG. 5, taken along line 6-6 of FIG. 5.

FIGS. 6-12 show various components of shaft (130) that provide control for articulation of articulation section (136). In particular, these components include a separator (150), a first articulation band (160) with an associated drive member (162), and a second articulation band (170) with an associated drive member (172). As best seen in FIG. 6, separator (150) includes an upper lumen (151), a middle lumen (152), and a lower lumen (153). Separator (150) also includes side recesses (154), a distal projection (156), and a gap (158). Separator (150) is disposed within cutting member driver tube (138) and maintains a fixed longitudinal position during operation of instrument (100). Thus, separator (150) and outer sheath (132) remain stationary relative to each other and relative to handpiece (120); while cutting member driver tube (138) reciprocates relative to separator (150), outer sheath (132), and handpiece (120). Distal projection (156) is configured to permit translation of driver block (139) substantially free from interference by distal projection (156) or by any other portion of separator (150).

In the present example, separator (150) is formed as two pieces arranged in an end-to-end configuration, with a distal projection from the proximal piece helping to define gap (158). Of course, separator (150) may alternatively be formed as a single piece or any other suitable number of pieces. By way of example only, gap (158) may be formed as a cutout from a single piece of material.

As will be described in greater detail below, a wire (900) extends through separator (150) to provide electrical communication to end effector (140). In particular, wire (900) extends through middle lumen (152) from the proximal end of separator (150) until wire (900) reaches gap (158). At gap (158), wire (900) transitions down to lower lumen (153), and extends through lower lumen (153) until reaching the distal end of separator (150). Wire (900) then extends across articulation section (136) to end effector (140). Wire (900) is thus operable to communicate power from a power source to end effector (140) in accordance with the teachings herein and in accordance with the teachings of various references cited herein. Distal projection (156) protects wire (900) from driver block (139), such that driver block (139) is unable to contact wire (900) regardless of the longitudinal position of driver block (139) along distal projection (156).

Figure 7:
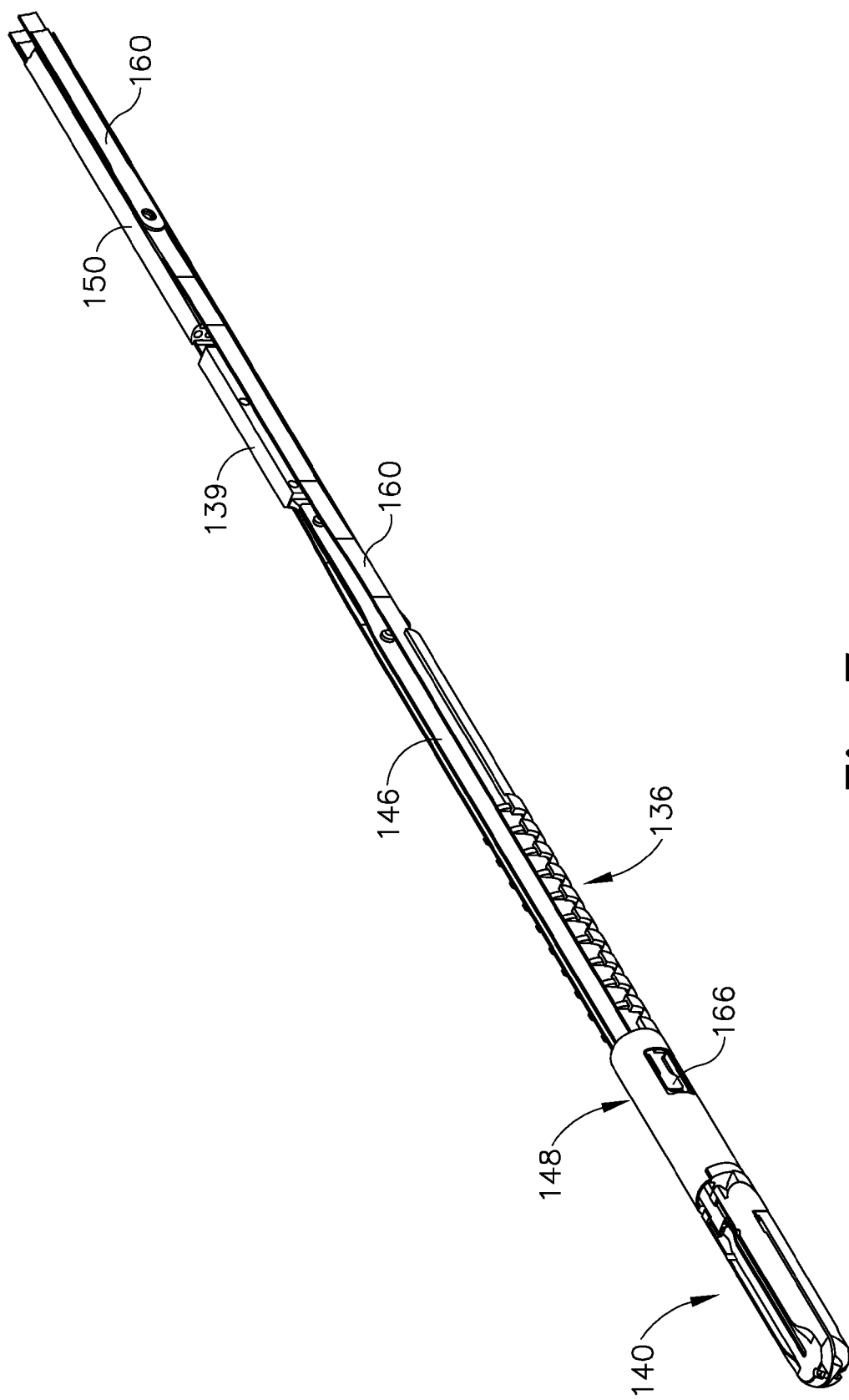
FIG. 7 depicts a perspective view of components of the shaft assembly and end effector of the device of FIG. 5.
Figure 8:
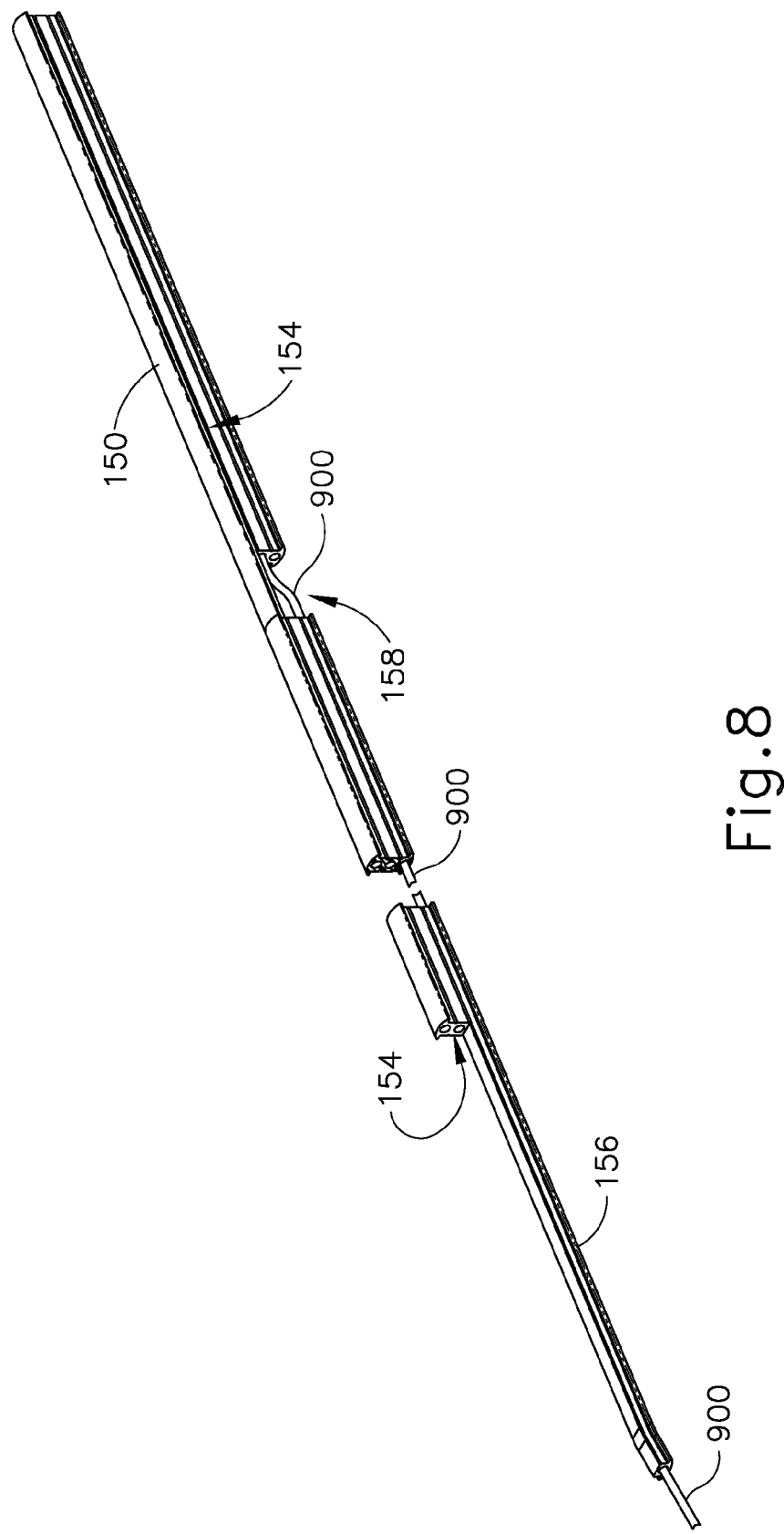
FIG. 8 depicts a perspective view of a support member of the shaft assembly of the device of FIG. 5.

First articulation band (160) is slidably disposed in one side recess (154) of separator (150) while second articulation band (170) is slidably disposed in the other side recess (154) of separator (150). Referring back to FIG. 6, side recesses (154) include longitudinally extending grooves (155) that are configured to reduce the contact surface area with articulation bands (160, 170), thereby reducing friction between separator (150) and articulation bands (160, 170). Separator (150) may also be formed of a low friction material and/or include a surface treatment to reduce friction. Articulation bands (160, 170) both extend longitudinally along the entire length of shaft (130), including through articulation section (136). As shown in FIG. 7, the distal end (166) of first articulation band (160) is secured to one side of the proximal portion (148) of end effector (140) at an anchor point. The distal end (176) of second articulation band (170) is secured to the other side of proximal portion (148) of end effector (140) at an anchor point. As will be described in greater detail below, rotary articulation knob (128) is operable to selectively advance one articulation band (160, 170) distally while simultaneously retracting the other articulation band (160, 170) proximally, and vice-versa. It should be understood that this opposing translation will cause articulation section (136) to bend, thereby articulating end effector (140). In particular, end effector (140) will deflect toward whichever articulation band (160, 170) is being retracted proximally; and away from whichever articulation band (160, 170) is being advanced distally.

Figure 9:
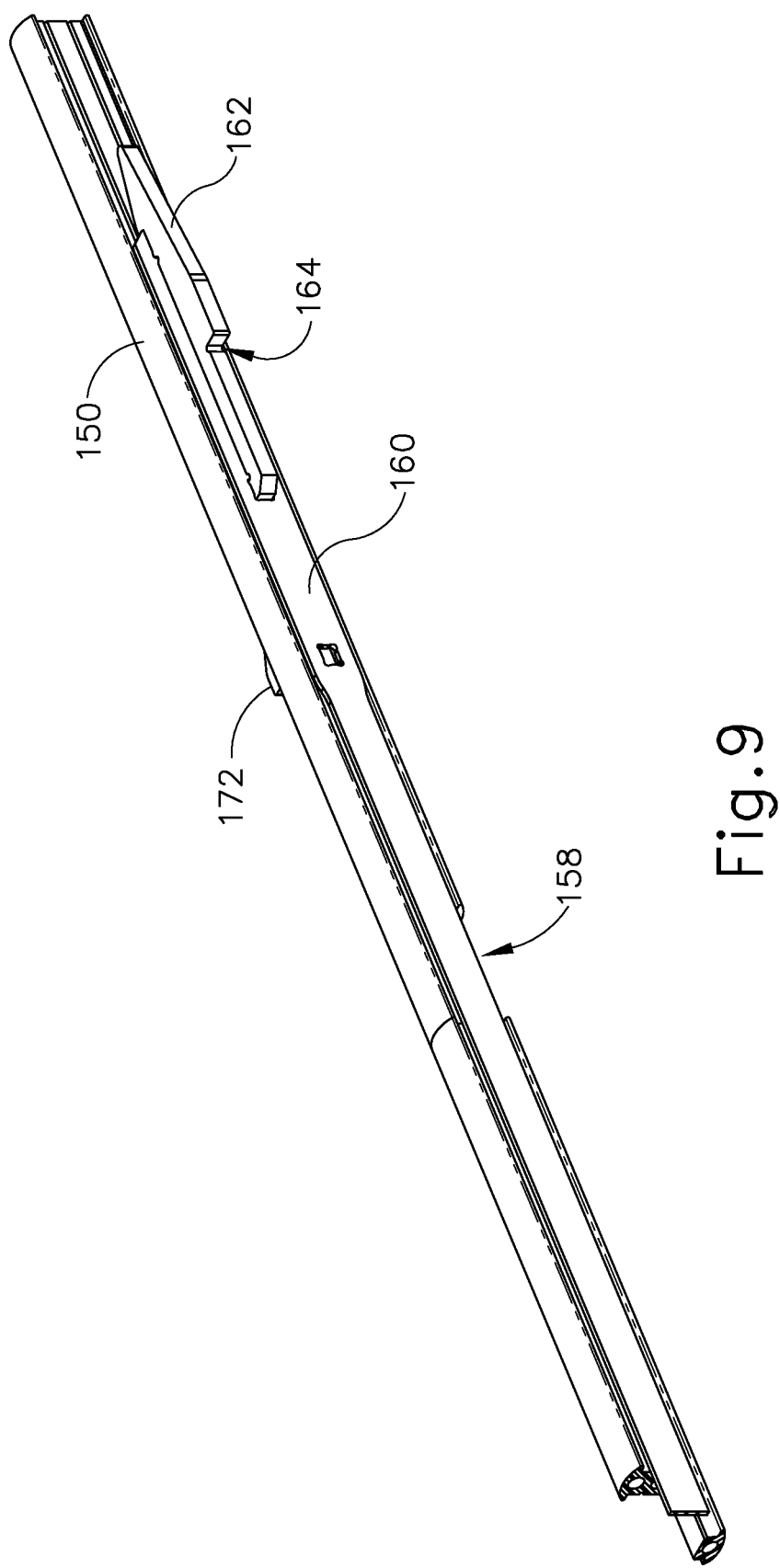
FIG. 9 depicts a partial perspective view of articulation control components of the device of FIG. 5, along one side of the support member.
Figure 10:
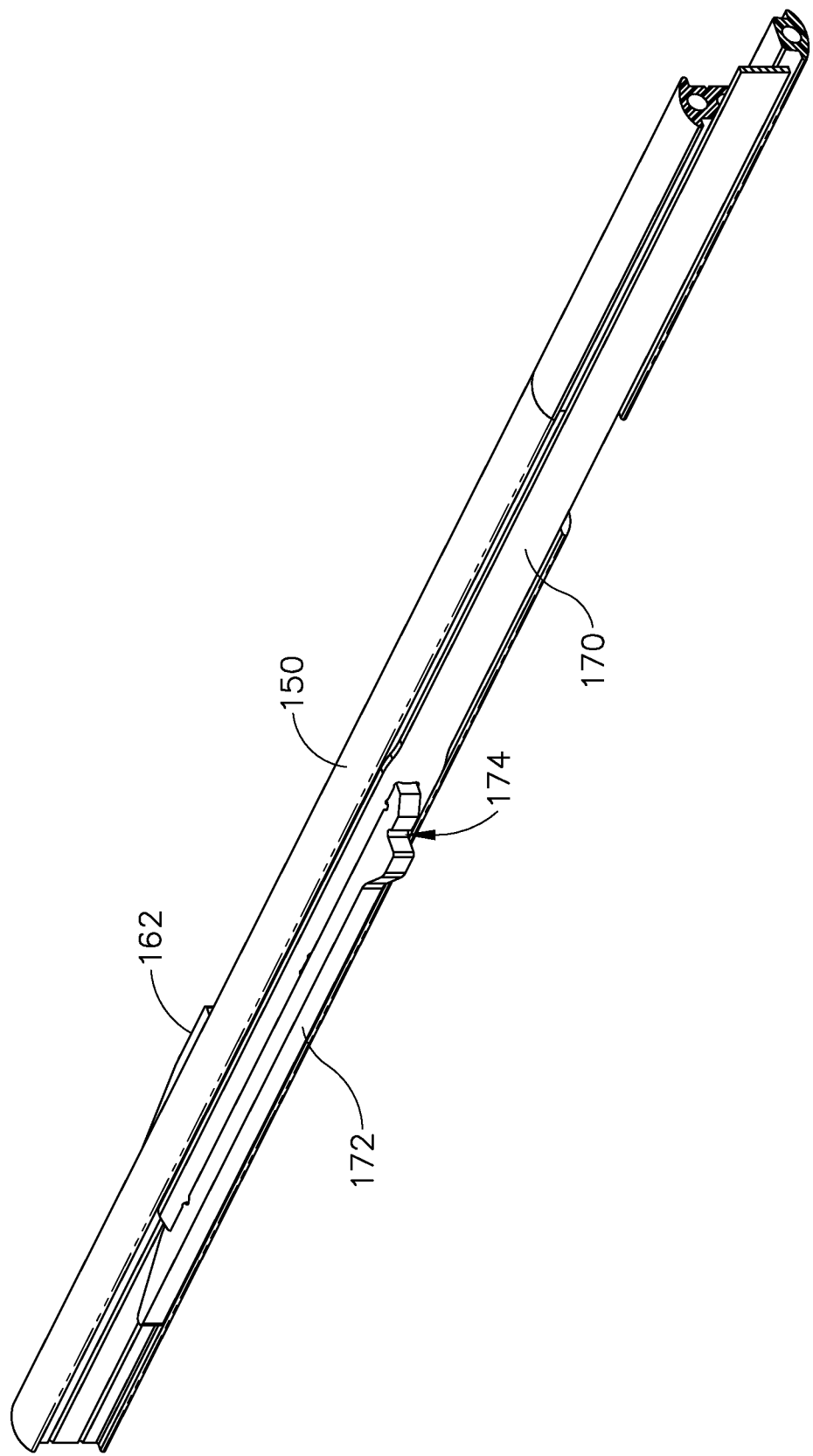
FIG. 10 depicts a partial perspective view of articulation control components of the device of FIG. 5, along another side of the support member.
Figure 11:
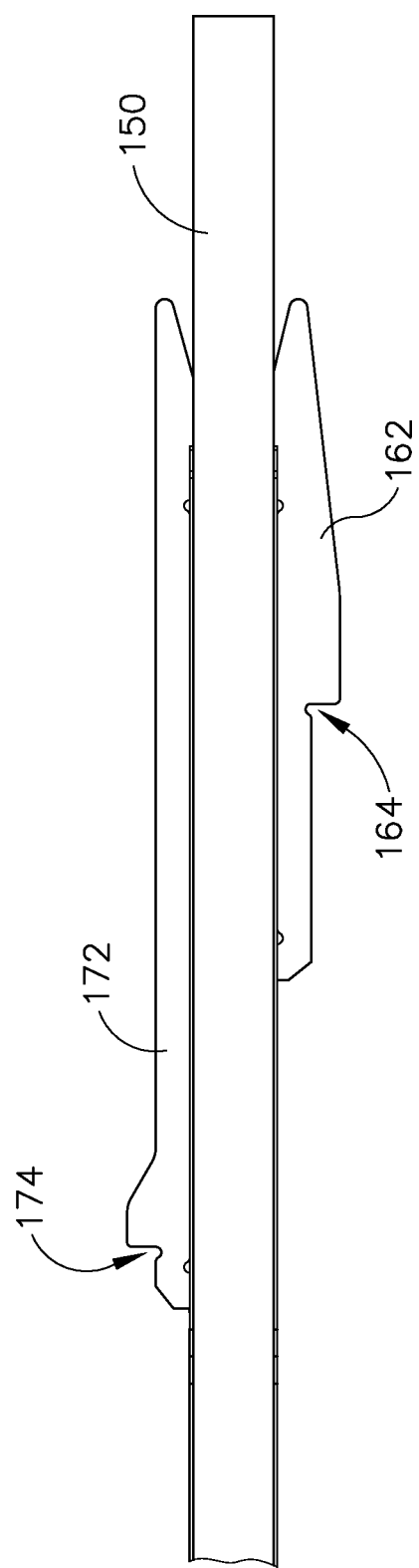
FIG. 11 depicts a top plan view of the articulation control components of FIGS. 9-10.
Figure 12:
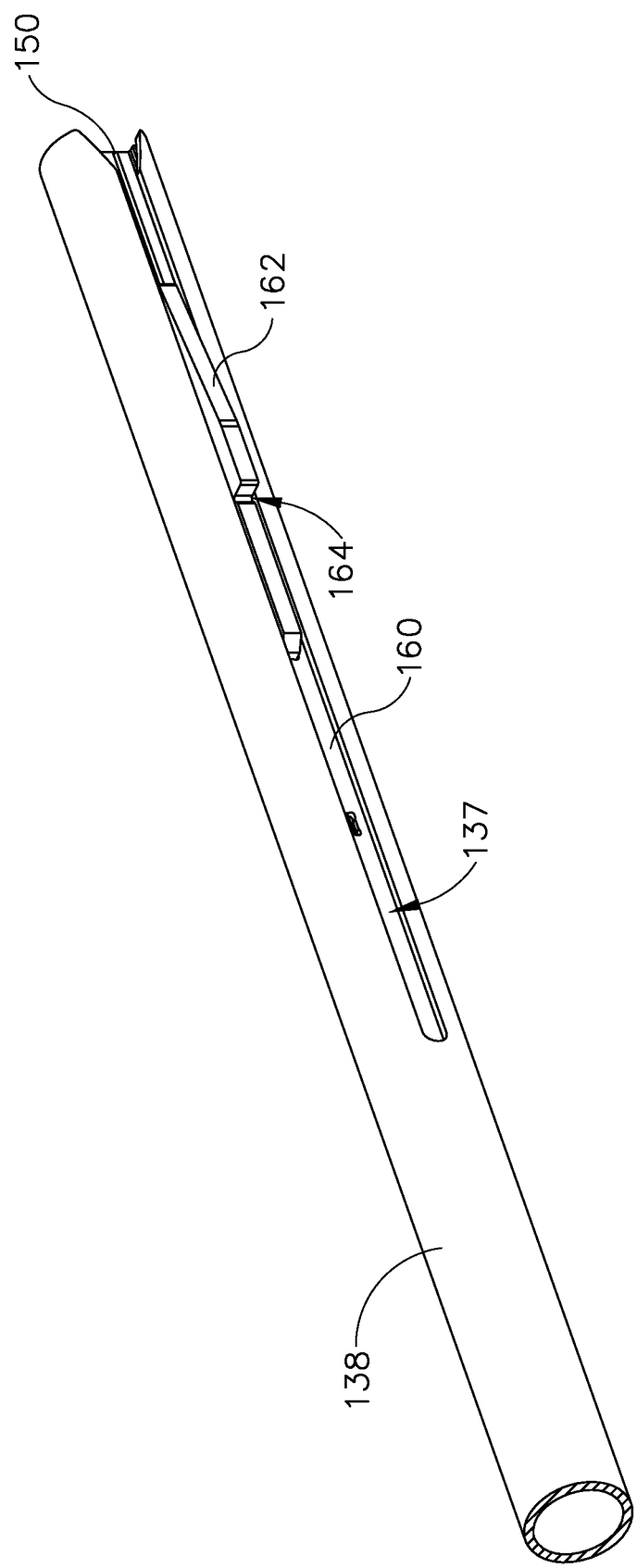
FIG. 12 depicts a partial perspective view of the articulation control components of FIG. 9 surrounded by a sheath.

As best seen in FIG. 9, drive member (162) is unitarily secured to articulation band (160) and includes a notch (164) extending laterally inwardly. As best seen in FIG. 10, drive member (172) is unitarily secured to articulation band (170) and includes a notch (174) extending laterally inwardly. As best seen in FIG. 11, drive members (162, 164) are spaced and configured such that notches (164, 174) are at different longitudinal positions along the length of separator (150). As best seen in FIG. 12, the proximal portion of cutting member driver tube (138) includes longitudinally extending slots (137). Drive members (162, 172) are slidably disposed in slots (137) and notches (164, 174) are radially positioned outside the outer circumference of cutting member driver tube (138). Slots (137) are configured to enable free translation of cutting member driver tube (138) relative to drive members (162, 172), to thus enable free actuation of cutting member (164) regardless of the articulation state of articulation section (136). In other words, slots (137) are configured to enable free translation of drive members (162, 172) relative to cutting member driver tube (138), to thus enable free articulation of articulation section (136) regardless of the longitudinal position of cutting member (164).

Figure 14:
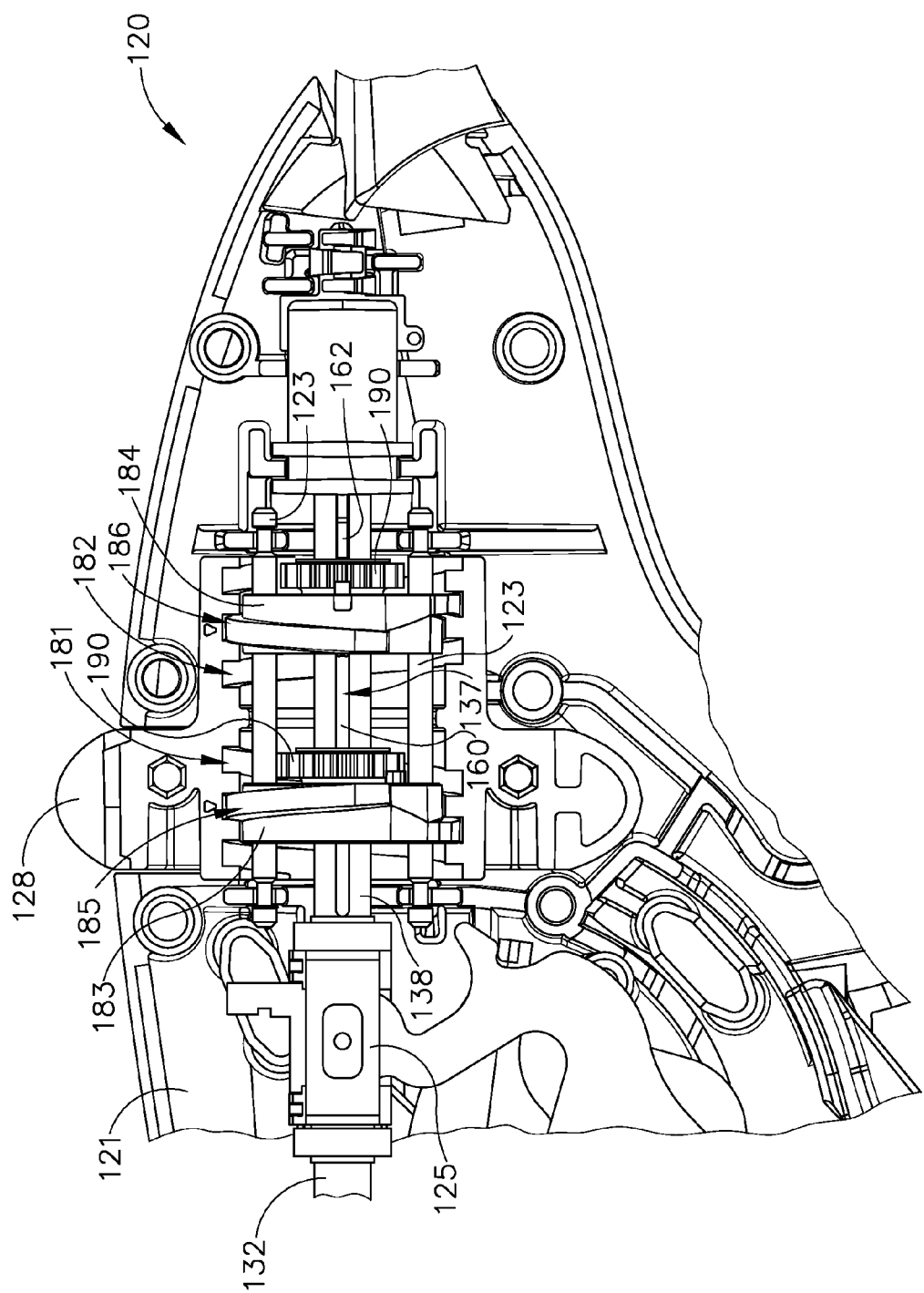
FIG. 14 depicts a side elevational view of articulation control components of the handle assembly of FIG. 13, with half of an articulation control knob body removed.

As shown in FIGS. 13-14, rotary articulation knob (128) is coaxially positioned about the proximal portion of driver tube (138) and encompasses drive members (162, 172). Articulation knob (128) is oriented perpendicular to the longitudinal axis defined by shaft (130) and is rotatable about the longitudinal axis defined by shaft (130). As will be described in greater detail below, such rotation of articulation knob (128) will cause opposing translation of drive members (162, 172), with the directions of such opposing translations depending on the direction in which articulation knob (128) is rotated, such that rotation of articulation knob (128) will articulate end effector (140). As shown in FIG. 14, articulation knob (128) includes a first internal threading (180) and a second internal threading (182). Threadings (181, 182) have opposing pitch angles or orientations in this example.

Figure 15:
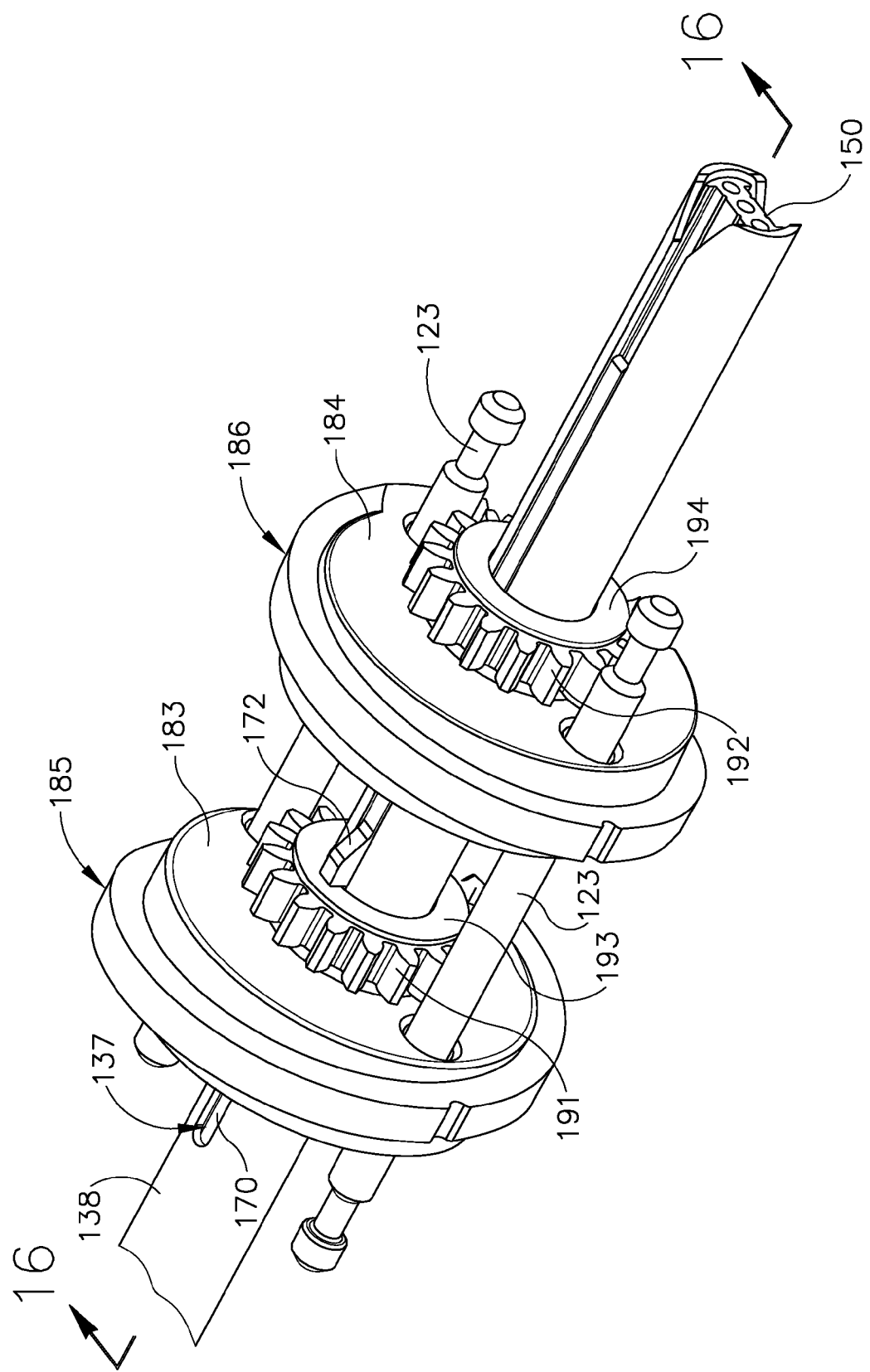
FIG. 15 depicts a perspective view of articulation control components of the handle assembly of FIG. 13, coupled with the articulation control components of FIGS. 9-10.

As best seen in FIGS. 14-15, a first lead screw (183) and a second lead screw (184) are slidably disposed along a pair of pins (123), which are secured to housing (121). Thus, lead screws (183, 184) are operable to translate within housing (121) but are prevented from rotating within housing (121). First lead screw (183) includes exterior threading (185) that is engaged with threading (181) of articulation knob (128); while second lead screw (184) includes exterior threading (186) that is engaged with threading (182) of articulation knob (128). The pitch angle of threading (185) complements the pitch angle of threading (181); while the pitch angle of threading (186) complements the pitch angle of threading (182). It should therefore be understood that, due to the opposing pitch angles, rotation of knob (128) in a first direction will drive lead screw (183) distally while simultaneously driving lead screw (184) proximally; and rotation of knob in a second direction will drive lead screw (183) proximally while simultaneously driving lead screw (184) distally.

The angles of threading (181, 182, 185, 186) are also configured such that articulation section (136) will be effectively locked in any given articulated position, such that transverse loads on end effector (140) will generally not bend articulation section (136), due to friction between threading (181, 182, 185, 186). In other words, articulation section (136) will only change its configuration when knob (128) is rotated. While the angles of threading may substantially prevent bending of articulation section (136) in response to transverse loads on end effector (140), the angles may still provide ready rotation of articulation knob (128) to translate lead screws (183, 184). By way of example only, the angles of threading (181, 182, 185, 186) may be approximately +/−2 degrees or approximately +/−3 degrees. Other suitable angles will be apparent to those of ordinary skill in the art in view of the teachings herein. It should also be understood that threading (181, 182, 185, 186) may have a square or rectangular cross-section or any other suitable configuration.

Figure 16:
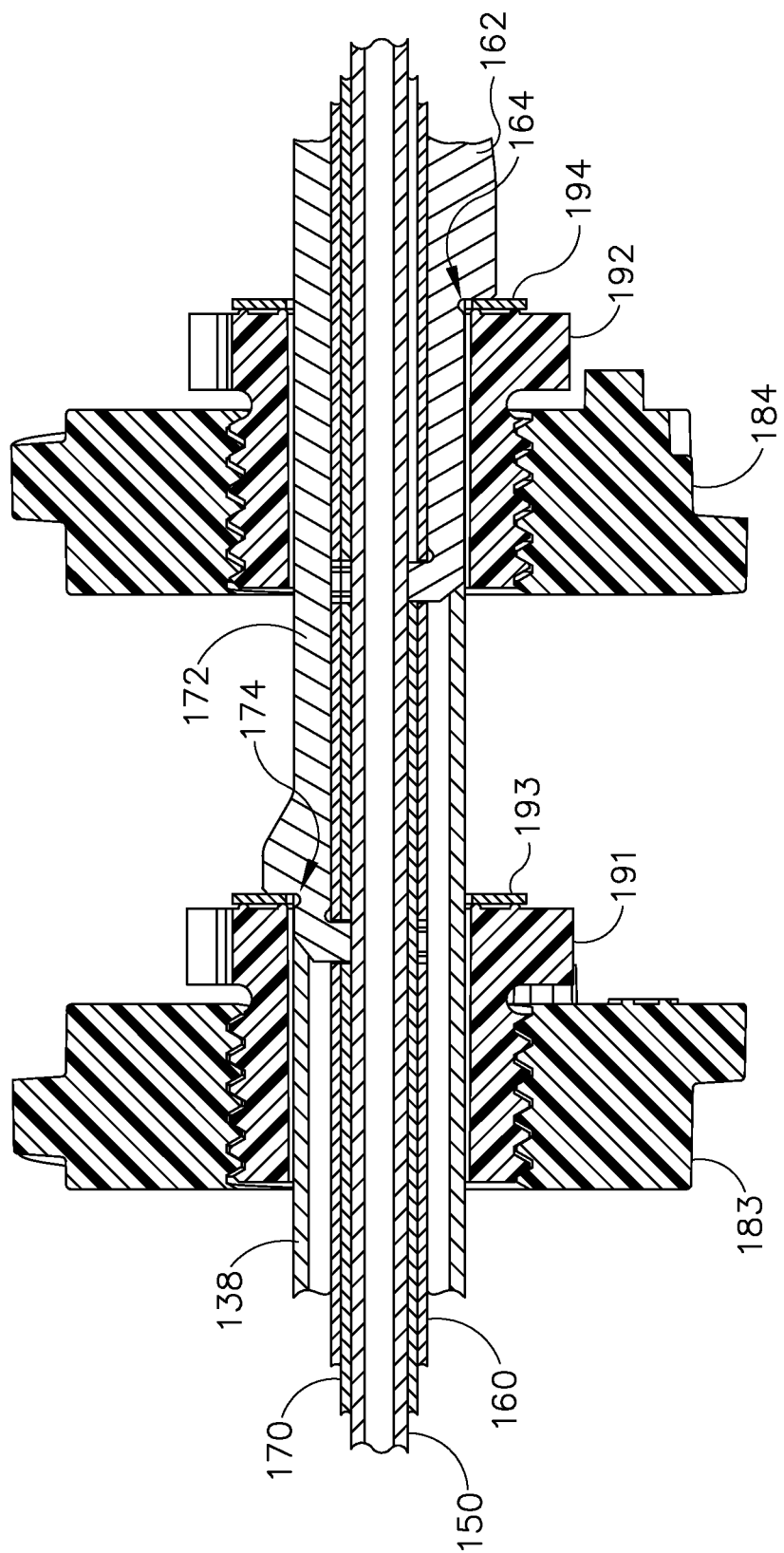
FIG. 16 depicts a side cross-sectional view of the articulation control components of FIG. 15, taken along line 16-16 of FIG. 15.

As best seen in FIGS. 15-16, a first tensioner gear (191) is threadably engaged with first lead screw (183); while a second tensioner gear (192) is threadably engaged with second lead screw (184). Thus, the longitudinal position of first tensioner gear (191) relative to first lead screw (183) may be adjusted by rotating first tensioner gear (191) relative to first lead screw (183); while the longitudinal position of second tensioner gear (192) relative to second lead screw (184) may be adjusted by rotating second tensioner gear (192) relative to second lead screw (184). Otherwise, first tensioner gear (191) will translate unitarily with first lead screw (183); while second tensioner gear (192) will translate unitarily with second lead screw (184).

First tensioner gear (191) is also engaged with a washer (193), which is further engaged with notch (174) of drive member (172). The engagement between washer (193) and drive member (172) is such that washer (193) and drive member (172) will translate together. In some versions, washer (193) is secured to tensioner gear (191) in such a manner that tensioner gear (191) both pulls washer (193) distally and pushes washer (193) proximally. Thus, in some such versions, first lead screw (183) is operable to both push articulation band (170) distally and pull articulation band (170) proximally, depending on which direction knob (128) is rotated. In the present example, however, tensioner gear (191) merely abuts washer (193), such that tensioner gear (191) is operable to push washer (193) proximally but cannot pull washer (193) distally. Thus, in the present example, first lead screw (183) is operable to pull articulation band (170) proximally but cannot actively push articulation band (170) distally. Instead, first lead screw (183) may simply pull tensioner gear (191) distally to enable articulation band (170), drive member (172), and washer (193) to be driven distally in response to proximal retraction of articulation band (160) as communicated through articulation section (136). Other suitable relationships will be apparent to those of ordinary skill in the art in view of the teachings herein. It should also be understood that drive member (172) and/or washer (193) may be rotatable relative to tensioner gear (191), which may permit rotation of shaft (130) by knob (134). As described in greater detail below, tensioner gear (191) may be used to take out any tolerance gaps between drive member (172) and lead screw (183).

Similarly, second tensioner gear (192) is engaged with a washer (194), which is further engaged with notch (164) of drive member (162). The engagement between washer (194) and drive member (162) is such that washer (194) and drive member (162) will translate together. In some versions, washer (194) is secured to tensioner gear (192) in such a manner that tensioner gear (192) both pulls washer (194) distally and pushes washer (194) proximally. Thus, in some such versions, second lead screw (184) is operable to both push articulation band (160) distally and pull articulation band (160) proximally, depending on which direction knob (128) is rotated. In the present example however, tensioner gear (192) merely abuts washer (194), such that tensioner gear (192) is operable to push washer (194) proximally but cannot pull washer (194) distally. Thus, in the present example, second lead screw (184) is operable to pull articulation band (160) proximally but cannot actively push articulation band (160) distally. Instead, second lead screw (184) may simply pull tensioner gear (192) distally to enable articulation band (160), drive member (162), and washer (194) to be driven distally in response to proximal retraction of articulation band (170) as communicated through articulation section (136). Other suitable relationships will be apparent to those of ordinary skill in the art in view of the teachings herein. It should also be understood that drive member (162) and/or washer (194) may be rotatable relative to tensioner gear (192), which may permit rotation of shaft (130) by knob (134). As described in greater detail below, tensioner gear (192) may be used to take out any tolerance gaps between drive member (162) and lead screw (184).

Figure 17A:
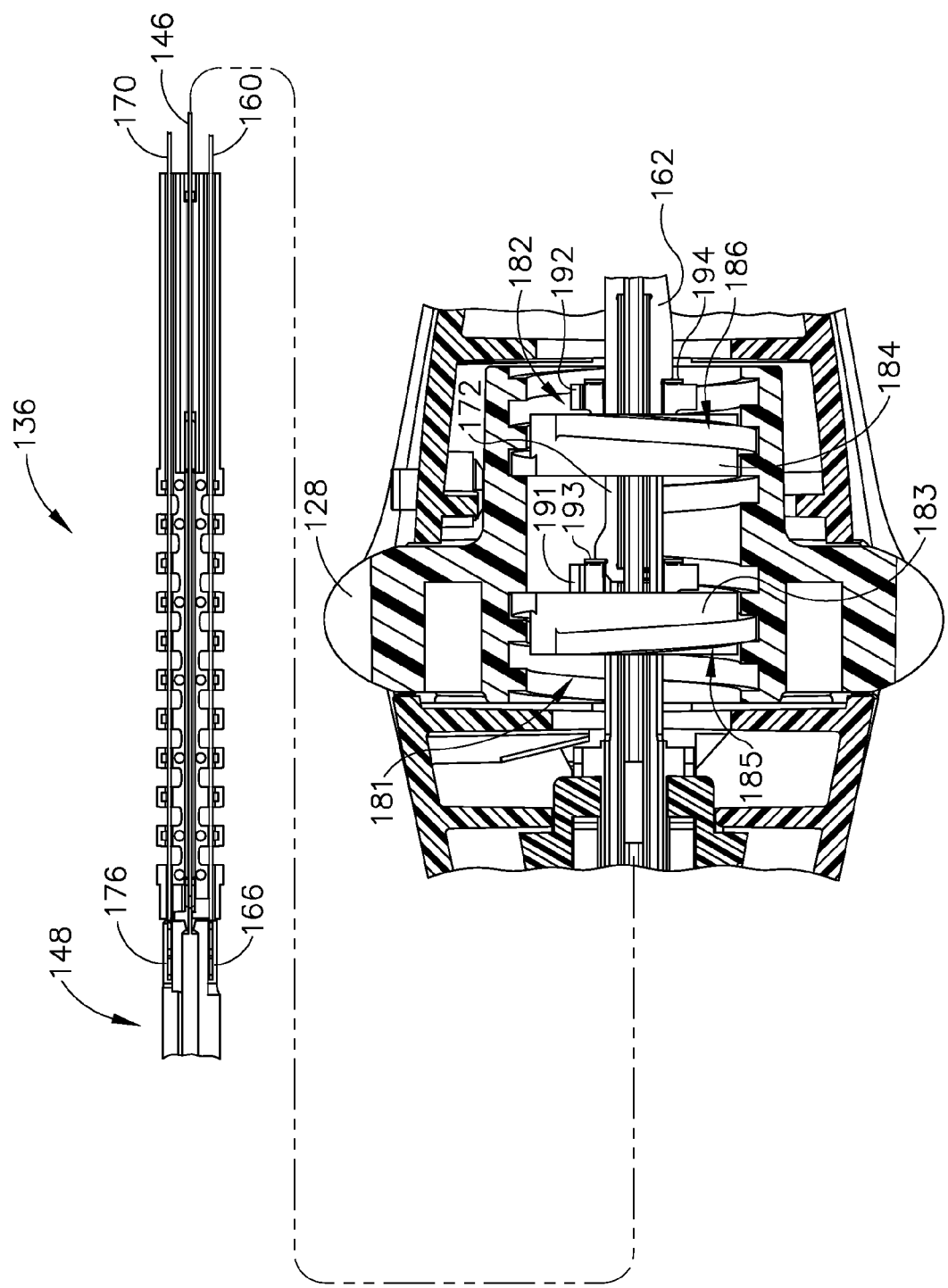
FIG. 17A depicts a partial cross-sectional view of articulation control components and the articulation section of the shaft of the device of FIG. 5, with the articulation section in a substantially straight configuration.
Figure 17B:
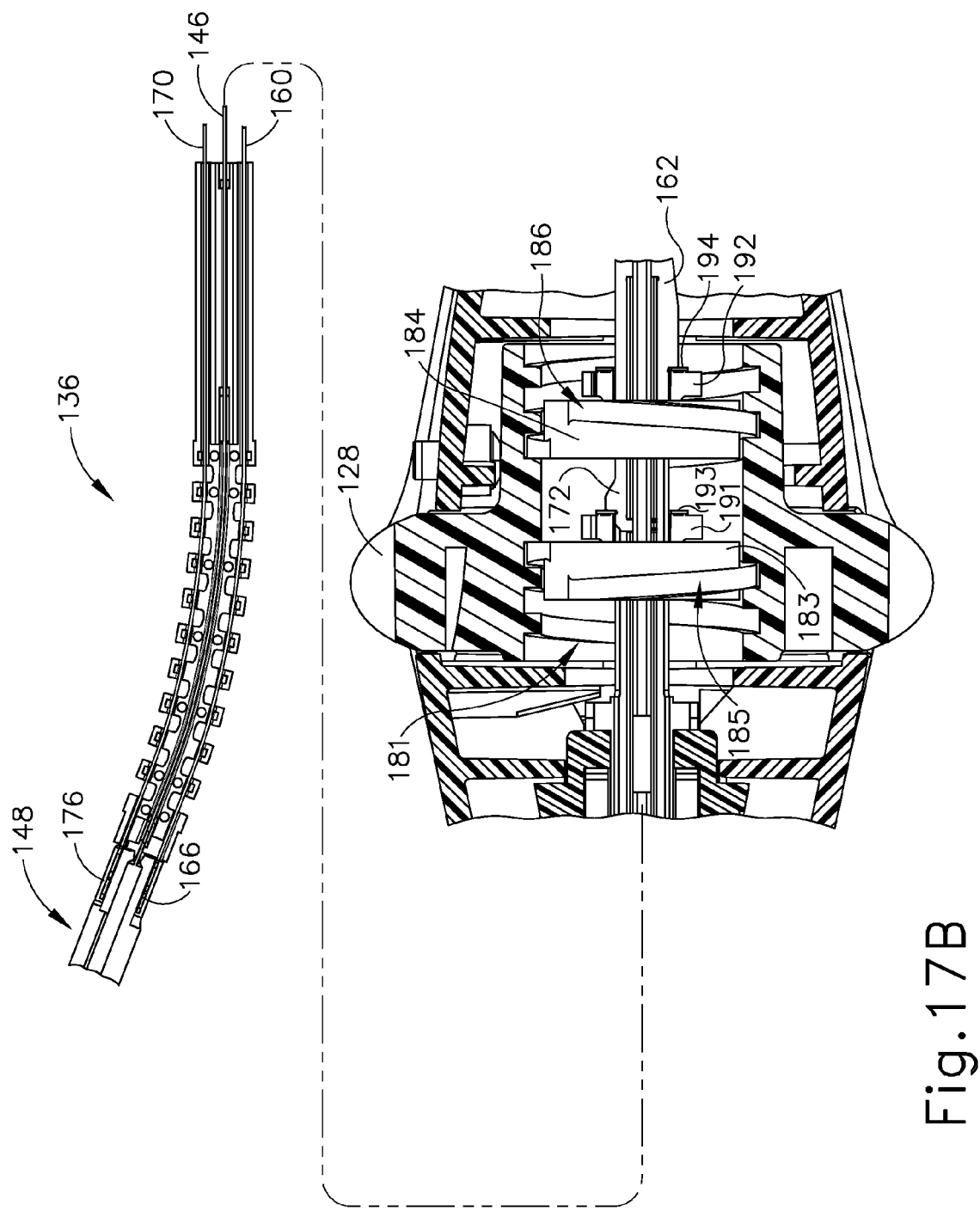
FIG. 17B depicts a partial cross-sectional view of the components of FIG. 17A, with the articulation section in a first stage of articulation.
Figure 17C:
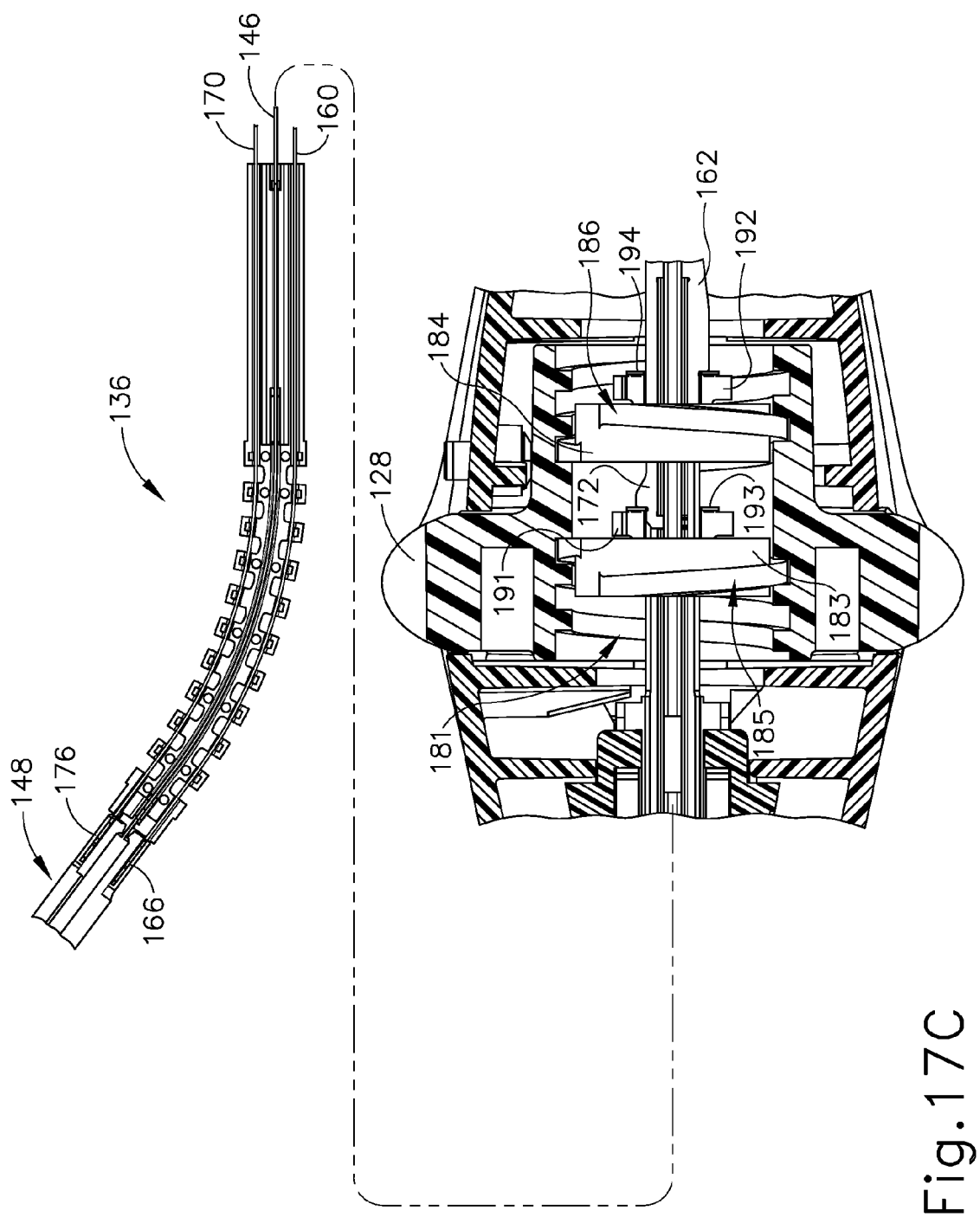
FIG. 17C depicts a partial cross-sectional view of the components of FIG. 17A, with the articulation section in a second stage of articulation.

FIGS. 17A-17C show several of the above described components interacting to bend articulation section (136) to articulate end effector (140). In FIG. 17A, articulation (136) is in a substantially straight configuration. Then, knob (128) is rotated, which causes lead screw (183) to translate proximally and lead screw (184) to advance distally. This proximal translation of lead screw (183) pulls articulation band (170) proximally, which causes articulation section (136) to start bending as shown in FIG. 17B. This bending of articulation section (136) pulls articulation band (160) distally. The distal advancement of lead screw (184) in response to rotation of knob (128) enables articulation band (160) and drive member (162) to advance distally. In some other versions, the distal advancement of lead screw (184) actively drives drive member (162) and articulation band (160) distally. As the user continues rotating knob (128), the above described interactions continue in the same fashion, resulting in further bending of articulation section (136) as shown in FIG. 17C. It should be understand that rotating knob (128) in the opposite direction will cause articulation section (136) to straighten, and further rotation in the opposite direction will cause articulation section (136) to bend in the opposite direction.

In some versions, knob (128) includes a visual indicator that is associated with articulation section (136) being in a substantially straight configuration. Such a visual indicator may align with a corresponding visual indicator on housing (121) of handpiece (120). Thus, when a user has rotated knob (128) to make articulation section (136) approach a substantially straight configuration, the user may observe such indicators to confirm whether articulation section (136) has in fact reached a substantially straight configuration. By way of example only, this may be done right before instrument (100) is withdrawn from a trocar to reduce the likelihood of articulation section (136) snagging on a distal edge of the trocar. Of course, such indicators are merely optional.

In some instances, manufacturing inconsistencies may result in articulation bands (160, 170) having slightly different lengths. In addition or in the alternative, there may be inherent manufacturing related inconsistencies in the initial positioning of lead screws (183, 184) relative to articulation knob (128), inconsistencies in the initial positioning of tensioner gears (191, 192) relative to lead screws (183, 184), and/or other inconsistencies that might result in undesirable positioning/relationships of articulation bands (160, 170). Such inconsistencies may result in lost motion or slop in the operation of the articulation features of instrument (100). To address such issues, tensioner gears (191, 192) may be rotated relative to lead screws (183, 184) to adjust the longitudinal position of drive members (162, 172) relative to lead screws (183, 184). For instance, if there is insufficient tension in articulation band (170), tensioner gear (191) may be rotated to drive washer (193) and drive member (172) proximally until articulation band (170) reaches a sufficient degree of tension. Similarly, if there is insufficient tension in articulation band (160), tensioner gear (192) may be rotated to drive washer (195) and drive member (162) proximally until articulation band (160) reaches a sufficient degree of tension. Lead screws (183, 184) may remain substantially stationary during such adjustments. Articulation section (136) may remain substantially straight during such adjustments and may even be held substantially straight during such adjustments.

In some versions, tensioner gears (191, 192) are rotated manually. In some other versions, tensioner gears (191, 192) are rotated automatically by a rack or other gear. In some such automated calibration systems, a control logic may monitor the load on a motor that is being used to drive a calibrating rack or gear that is engaged with tensioner gear (191, 192), and may automatically stop driving such a rack or gear when the load reaches a threshold associated with proper tensioning of band (160, 170). For instance, in cases where manufacturing inconsistencies or tolerance provide an initial gap between tensioner gears (191, 192) and washers (193, 194), or between washers (193, 194) and drive members (162, 172), tensioner gears (191, 192) may be rotated until such gaps are closed and sufficient contact is made between previously gapped components. As another merely illustrative variation, tensioner gears (191, 192) may be automatically stopped when the proximal ends of bands (160, 170) and/or drive members (162, 172) reach a certain point. Various suitable ways in which tensioner gears (191, 192) may be adjusted will be apparent to those of ordinary skill in the art in view of the teachings herein. It should also be understood that tensioner gears (191, 192) may be heat staked, glued, welded, or otherwise bonded to the respective lead screws (183, 184) when the gaps between drive members (162, 172) and their respective washers (193, 194) reach zero. Such bonding may prevent subsequent movement of tensioner gears (191, 192) relative to their respective lead screws (183, 184).

As another merely illustrative example, manufacturing inconsistencies may be addressed at the distal ends of bands (160, 170). For instance, before the distal ends of bands (160, 170) are secured to the proximal portion (148) of end effector (140), articulation section (136) may be held in a straight configuration and bands (160, 170) may be pulled distally to remove any slack in bands (160, 170). With bands (160, 170) both being in tension, bands (160, 170) may then be welded or otherwise secured to proximal portion (148) of end effector (140). It should be understood that this form of calibration is not limited to instrument (100), such that this form of calibration may be readily applied to various other instruments described herein, among others. Other suitable structures and methods for calibration will be apparent to those of ordinary skill in the art in view of the teachings herein.

Figure 18:
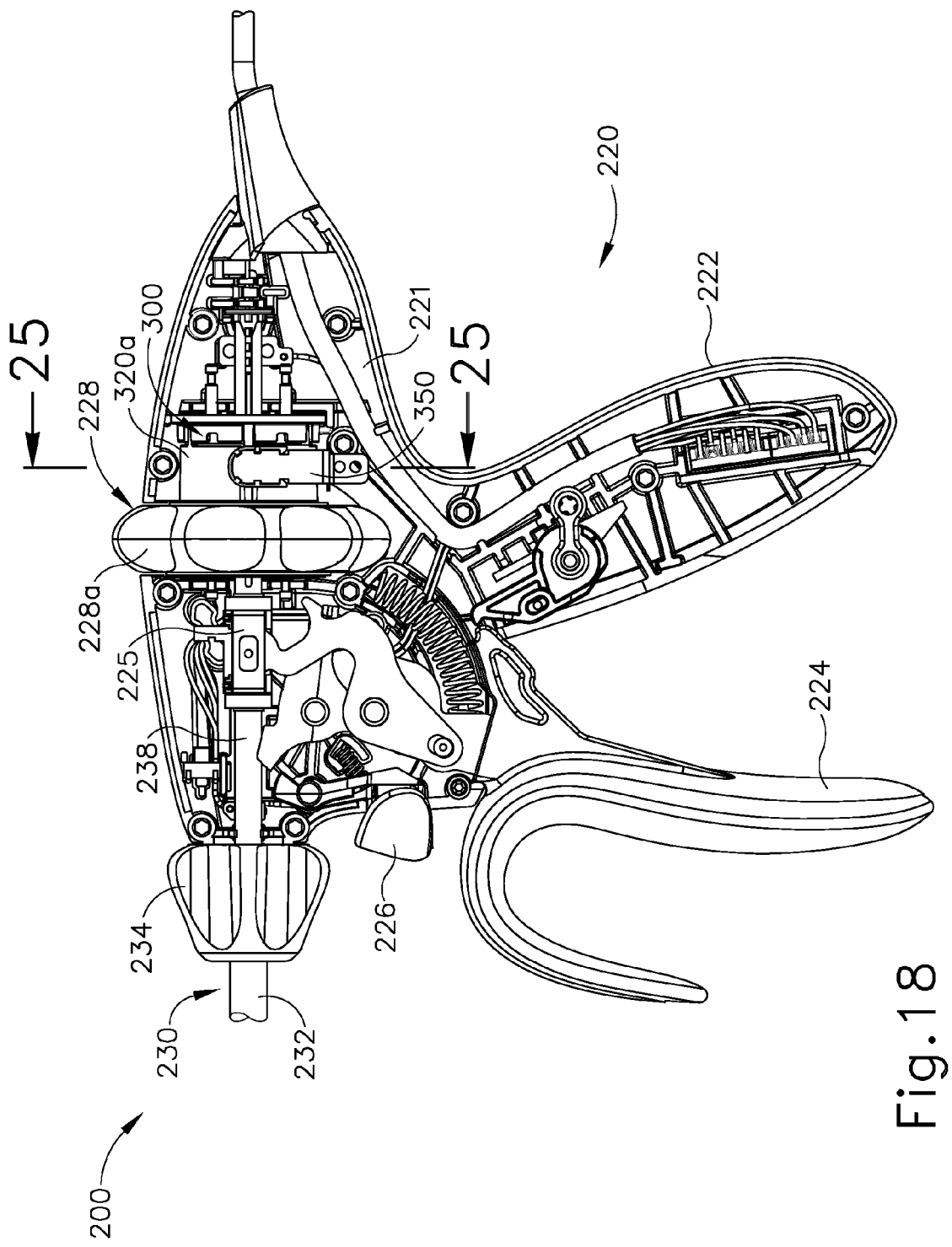
FIG. 18 depicts a side elevational view of the handle assembly of an exemplary alternative electrosurgical medical device with an articulation control knob.

B. Exemplary Articulation Control with Perpendicular Rotary Knob and Containment Rings FIG. 18 depicts an exemplary alternative electrosurgical instrument (200) that includes a handpiece (220), a shaft (230) extending distally from handpiece (220), and an end effector (not shown) disposed at a distal end of shaft (230). The end effector of instrument (200) is substantially identical to end effector (140) of instrument (100) described above. Handpiece (220) of the present example includes a pistol grip (222), a pivoting trigger (224), an activation button (226), and a rotary articulation knob (228). Trigger (224) is pivotable toward and away from pistol grip (222) to selectively actuate the end effector as described above and as described in one or more of the references cited herein. Activation button (226) is operable to selectively activate RF circuitry that is in communication with the end effector, as also described above and as described in one or more reference cited herein. In some versions, activation button (226) also serves as a mechanical lockout against trigger (224), such that trigger (224) cannot be fully actuated unless button (226) is being pressed simultaneously. Examples of how such a lockout may be provided are disclosed in one or more of the references cited herein. It should be understood that pistol grip (222), trigger (224), and button (226) may be modified, substituted, supplemented, etc. in any suitable way, and that the descriptions of such components herein are merely illustrative. Articulation knob (228) of the present example is operable to selectively control an articulation section (not shown) of shaft (230), as will be described in greater detail below. The articulation section of shaft (230) is substantially identical to articulation section (136) of instrument (100) described above.

Figure 19:
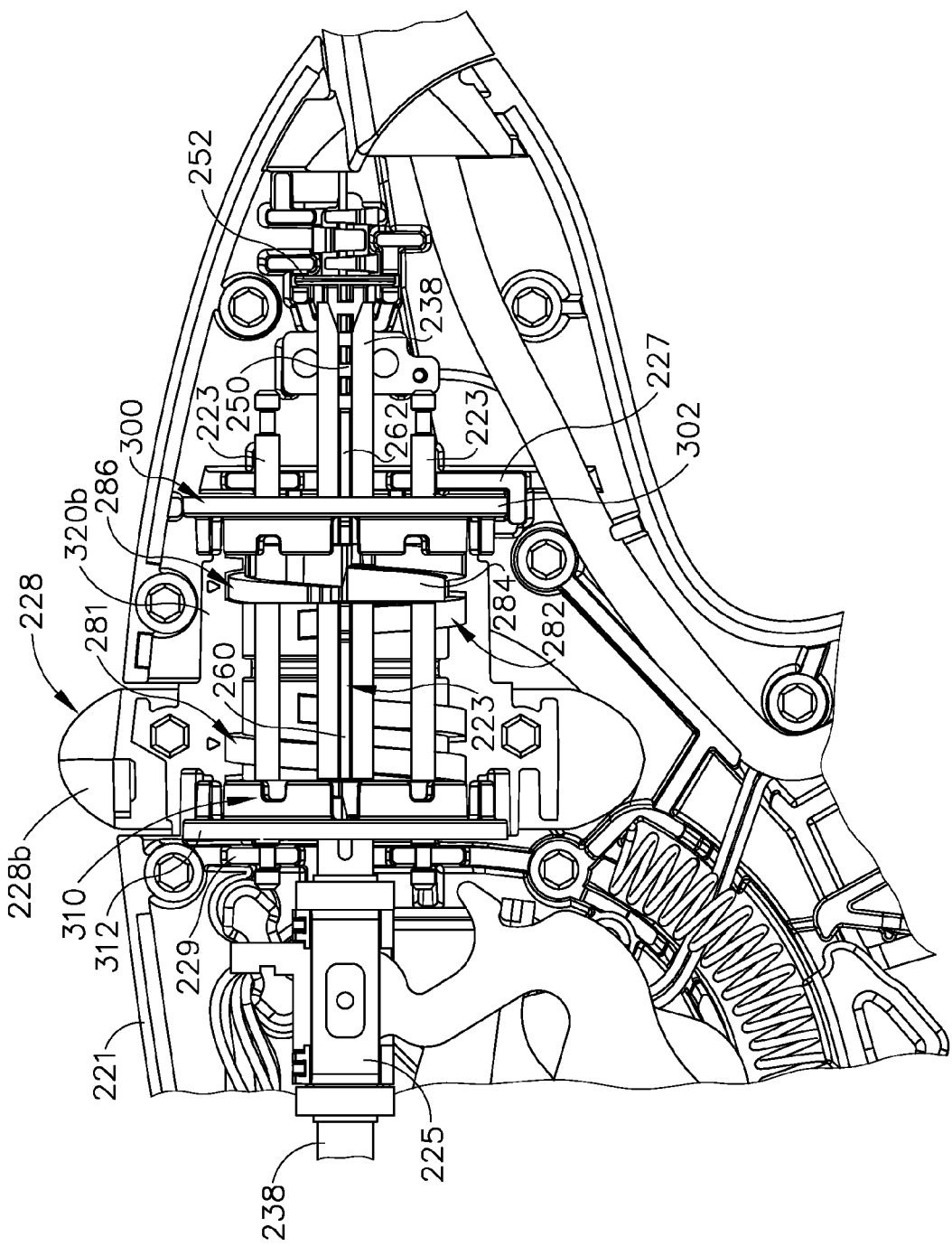
FIG. 19 depicts a side elevational view of articulation control components of the handle assembly of FIG. 18, with half of an articulation control knob body removed.

Shaft (230) of the present example includes an outer sheath (232), the above-noted articulation section (not shown) at the distal end of sheath (232), and a cutting member driver tube (238) that is slidably and coaxially disposed within sheath (232). Cutting member driver tube (238) is secured to a driver block (not shown, but substantially similar to driver block (139) described above), which is further secured to a cutting member (not shown, but substantially similar to cutting member (146) described above) of the above-noted end effector. Cutting member driver tube (238) is movable longitudinally to drive the driver block longitudinally, to thereby move the cutting member longitudinally. In the present example, driver tube (238) is advanced distally by squeezing trigger (224) toward pistol grip (222); while driver tube (238) is retracted proximally by releasing trigger (224) and/or by actively moving trigger (224) away from pistol grip (222). As shown in FIGS. 18-19, a yoke (225) couples trigger (224) with driver tube (238). Of course, the cutting member may be moved in any other suitable fashion. The articulation section of the present example is operable to selectively position the end effector at various angles relative to the longitudinal axis defined by sheath (232). Various examples of forms that an articulation section and other components of shaft (230) may take are described in various references cited herein, while further examples will be apparent to those of ordinary skill in the art in view of the teachings herein. Similarly, the end effector may be configured in accordance with end effector (40, 140) described above, in accordance with the teachings of various references cited herein, and/or in any other suitable way as will be apparent to those of ordinary skill in the art in view of the teachings herein.

FIGS. 18-24 show various components of shaft (230) that provide control for articulation of articulation section (236). In particular, these components include a separator (250), a first articulation band (260) with an associated drive member (262), and a second articulation band (270) with an associated drive member (272). Separator (250) of this example is substantially identical to separator (150) described above. However, one difference between separator (250) of this example and separator (150) described above is that separator (250) includes a proximal flange (252) that is engaged with housing (221), to prevent longitudinal movement of separator (250) relative to housing (221), as best seen in FIGS. 19-22. Like separator (150) described above, separator (250) is disposed within cutting member driver tube (238) and maintains a fixed longitudinal position during operation of instrument (200). Thus, separator (250) and outer sheath (232) remain stationary relative to each other and relative to handpiece (220); while cutting member driver tube (238) reciprocates relative to separator (250), outer sheath (232), and handpiece (220).

First articulation band (260) is slidably disposed in one side recess of separator (250) while second articulation band (270) is slidably disposed in the other side recess of separator (250). Articulation bands (260, 270) both extend longitudinally along the entire length of shaft (230), including through the articulation section. In particular, the distal end of first articulation band (260) is secured to one side of the proximal portion of the end effector at an anchor point. The distal end of second articulation band (270) is secured to the other side of the proximal portion of the end effector at an anchor point. As will be described in greater detail below, rotary articulation knob (228) is operable to selectively advance one articulation band (260, 270) distally while simultaneously retracting the other articulation band (260, 270) proximally, and vice-versa. It should be understood that this opposing translation will cause the articulation section to bend, thereby articulating the end effector. In particular, the end effector will deflect toward whichever articulation band (260, 270) is being retracted proximally; and away from whichever articulation band (260, 270) is being advanced distally.

Figure 22:
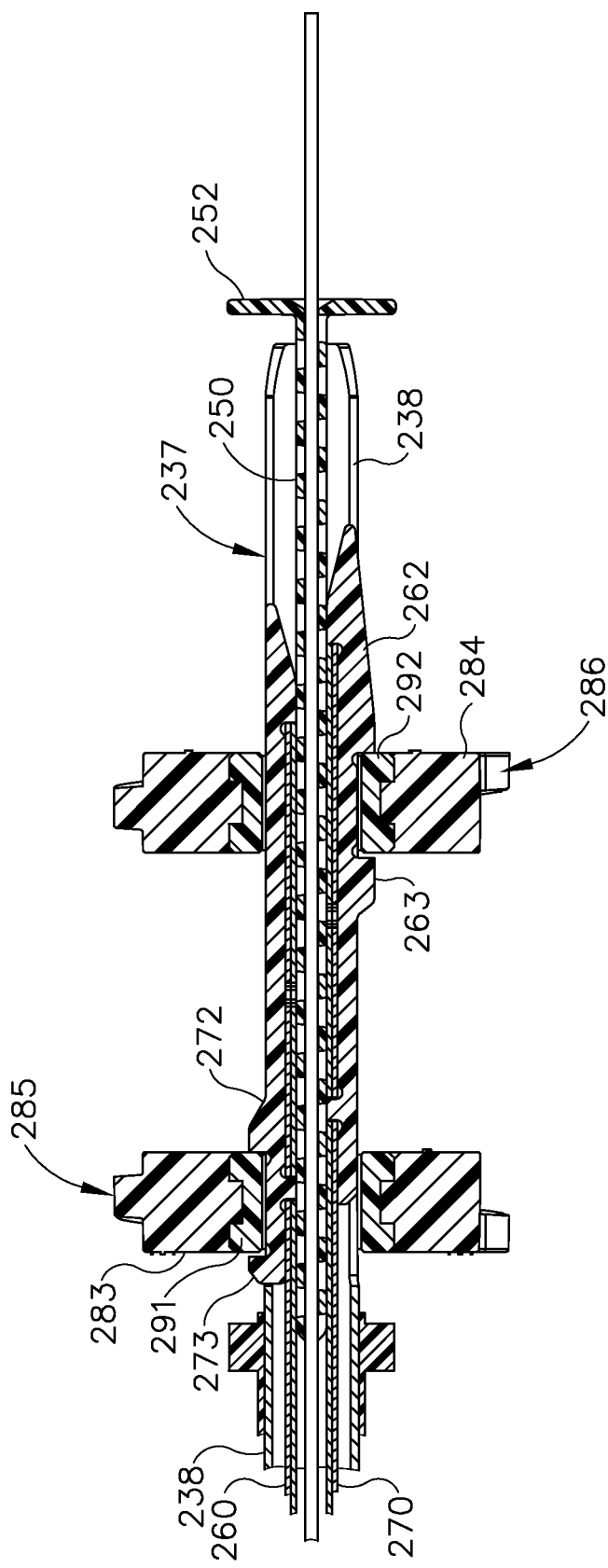
FIG. 22 depicts a top cross-sectional view of the articulation control components of FIG. 21, taken along line 22-22 of FIG. 21.

As best seen in FIG. 22, drive member (262) is unitarily secured to articulation band (260) and defines a lateral notch (264). Similarly, drive member (272) is unitarily secured to articulation band (270) and defines a lateral notch (274). Drive members (262, 264) are spaced and configured such that notches (264, 274) are at different longitudinal positions along the length of separator (250). As best seen in FIG. A. 21-22, the proximal portion of cutting member driver tube (238) includes longitudinally extending slots (237). Drive members (262, 272) are slidably disposed in slots (237) and notches (264, 274) are radially positioned outside the outer circumference of cutting member driver tube (238). Slots (237) are configured to enable free translation of cutting member driver tube (238) relative to drive members (262, 272), to thus enable free actuation of the cutting member regardless of the articulation state of the articulation section. In other words, slots (237) are configured to enable free translation of drive members (262, 272) relative to cutting member driver tube (238), to thus enable free articulation of the articulation section regardless of the longitudinal position of the cutting member.

Figure 20:
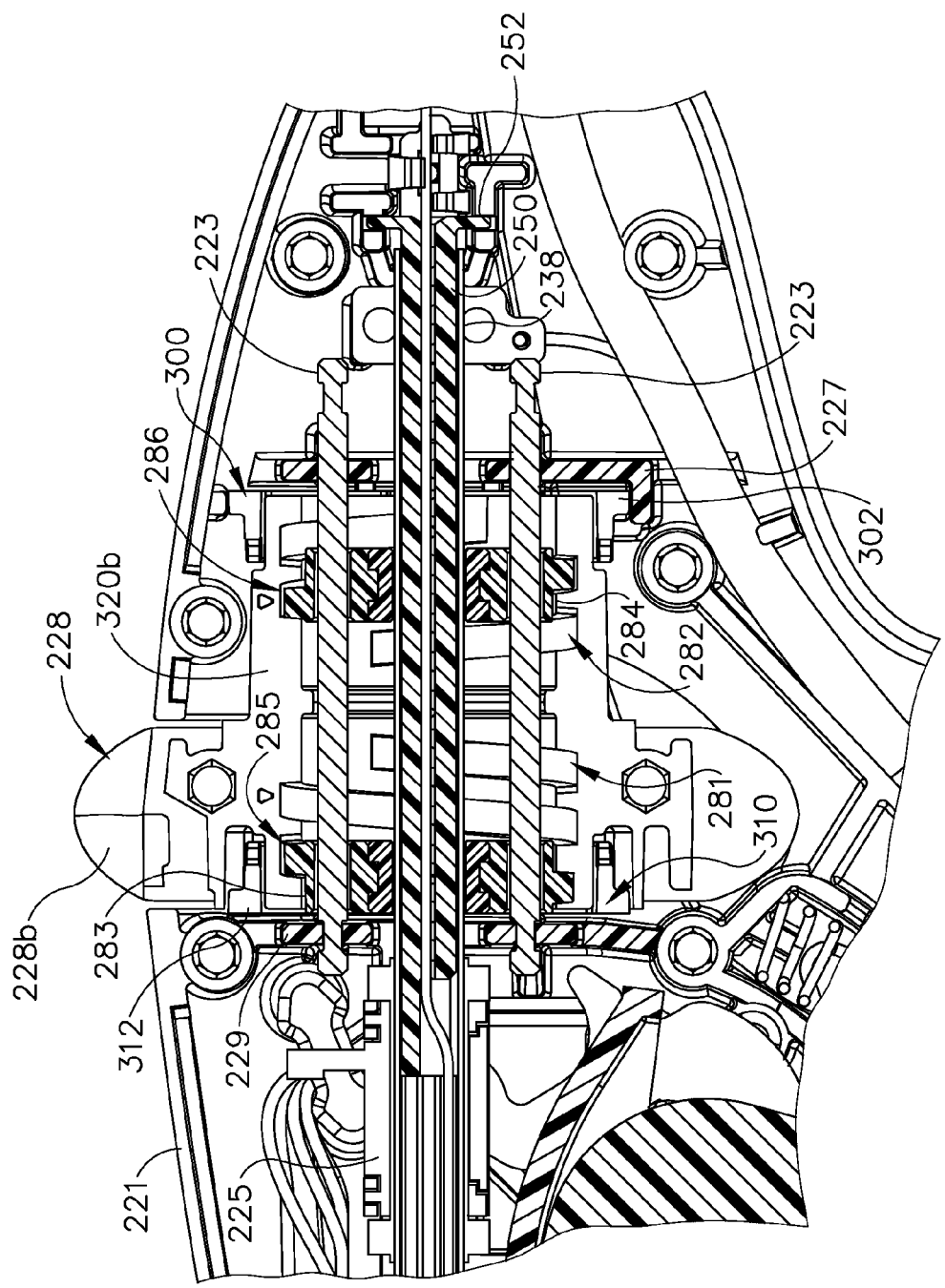
FIG. 20 depicts a side cross-sectional view of articulation control components of the handle assembly of FIG. 18.

As shown in FIGS. 18-20, rotary articulation knob (228) is coaxially positioned about the proximal portion of driver tube (238) and encompasses drive members (262, 272). Articulation knob (228) is formed by a first knob half (228a) and a second knob half (228b). Articulation knob (228) is oriented perpendicular to the longitudinal axis defined by shaft (230) and is rotatable about the longitudinal axis defined by shaft (230). As will be described in greater detail below, such rotation of articulation knob (228) will cause opposing translation of drive members (262, 272), with the directions of such opposing translations depending on the direction in which articulation knob (228) is rotated, such that rotation of articulation knob (228) will articulate the end effector.

Figure 23:
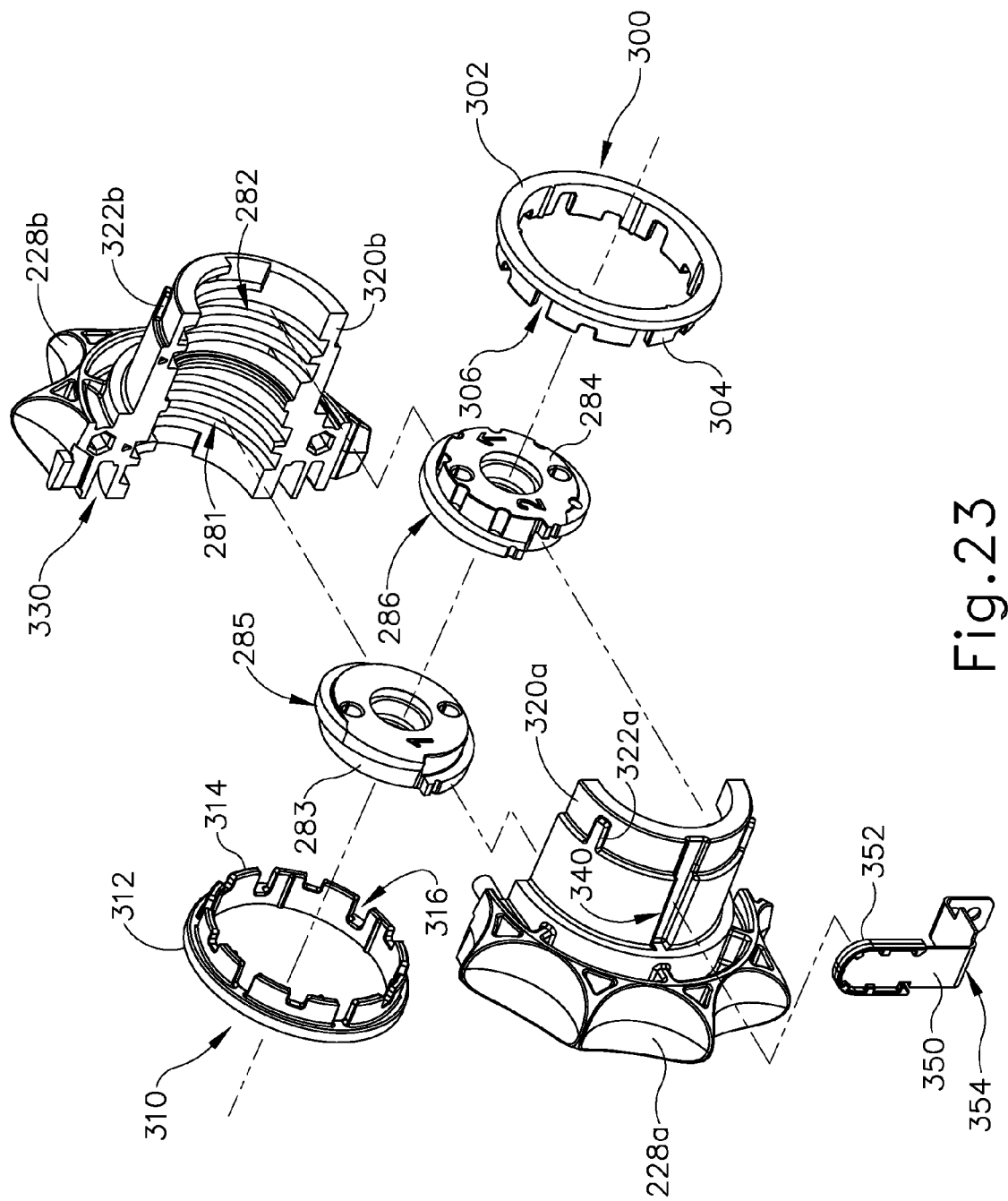
FIG. 23 depicts an exploded perspective view of some of the articulation control components of the handle assembly of FIG. 18.

As best seen in FIG. 23, articulation knob (228) includes a first internal threading (280) and a second internal threading (282). Threadings (281, 282) have opposing pitch angles or orientations in this example. It should be understood that threading (281) in first knob half (228a) is continuous with identical threading (281) in second knob half (228b) when halves (228a, 228b) are assembled together to form articulation knob (228). Likewise, threading (282) in first knob half (228a) is continuous with identical threading (282) in second knob half (228b) when halves (228a, 228b) are assembled together to form articulation knob (228). In some versions, an undercut in each section of threading (281, 282) is removed in order to facilitate manufacture of knob halves (228a, 228b) using injection molding processes. Of course, knob halves (228a, 228b) may be made using any other suitable process(es) and/or undercut in threading (281, 282) need not necessarily be removed.

Figure 21:
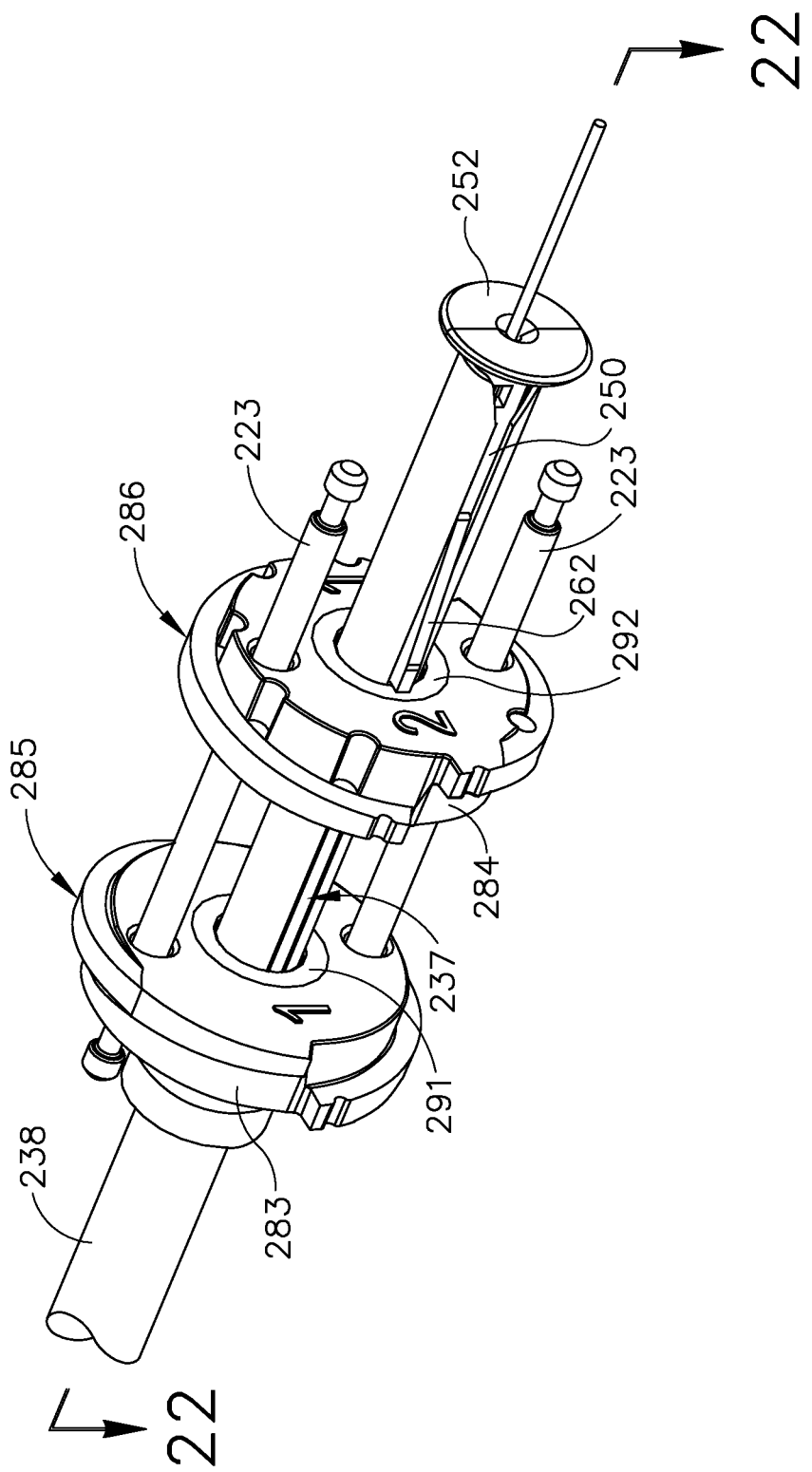
FIG. 21 depicts a perspective view of articulation control components of the handle assembly of FIG. 18.

As best seen in FIGS. 19-21, a first lead screw (283) and a second lead screw (284) are slidably disposed along a pair of pins (223), which are secured to housing (221). Lead screws (283, 284) are thus operable to translate within housing (221) along pins (223); but are prevented from rotating within housing (221). First lead screw (283) includes exterior threading (285) that is engaged with threading (281) of articulation knob (228); while second lead screw (284) includes exterior threading (286) that is engaged with threading (282) of articulation knob (228). The pitch angle of threading (285) complements the pitch angle of threading (281); while the pitch angle of threading (286) complements the pitch angle of threading (282). It should therefore be understood that, due to the opposing pitch angles, rotation of knob (228) in a first direction will drive lead screw (283) distally while simultaneously driving lead screw (284) proximally; and rotation of knob in a second direction will drive lead screw (283) proximally while simultaneously driving lead screw (284) distally. Threading (281, 282) may include hard stops at each end of threading (281, 282), to limit the longitudinal travel of lead screws (283, 284), which may in turn limit the degree of articulation that may be attained in the articulation section of shaft (230).

In the present example, the articulation section of shaft (230) is in a substantially straight configuration when lead screws (283, 284) are located at the approximate longitudinal center region of the corresponding threading (281, 282), such that rotation of knob (282) in a clockwise direction from this "home" position will deflect the end effector in a first direction away from the longitudinal axis of shaft (230); while rotation of knob (282) in a counterclockwise direction from the "home" position will deflect the end effector in a second direction away from the longitudinal axis of shaft (230). In some other versions, the articulation section of shaft (230) is in a substantially straight configuration when lead screws (283, 284) are located at opposite ends of the corresponding threading (281, 282), such that knob (282) will only rotate in one direction from this "home" position.

The angles of threading (281, 282, 285, 286) may be configured such that the articulation section will be effectively locked in any given articulated position, such that transverse loads on the end effector will generally not bend the articulation section, due to friction between threading (281, 282, 285, 286). In other words, threading (281, 282, 285, 286) is configured such that when a load is applied to the end effector, engagement in between threading (281, 282) and respective threading (285, 286) will not slip and cause the articulation state of the end effector to change. The articulation control assembly may thus be self-locking such that the articulation section will only change its configuration when knob (228) is rotated. While the angles of threading may substantially prevent bending of the articulation section in response to transverse loads on the end effector, the angles may still provide ready rotation of articulation knob (228) to translate lead screws (283, 284). By way of example only, the angles of threading (281, 282, 285, 286) may be approximately +/−2 degrees or approximately +/−3 degrees. Other suitable angles will be apparent to those of ordinary skill in the art in view of the teachings herein. It should also be understood that threading (281, 282, 285, 286) may have a square or rectangular cross-section or any other suitable configuration.

As best seen in FIG. 22, a first rivet member (291) is engaged with first lead screw (283); while a second rivet member (292) is engaged with second lead screw (284). First rivet member (291) is disposed in notch (274) of drive member (272). The engagement between first rivet member (291) and drive member (272) is such that first rivet member (291) and drive member (272) will translate together. In other words, first rivet member (291) both pulls drive member (272) proximally and pushes drive member (272) distally, depending on the direction in which knob (228) is rotated. Thus, first lead screw (283) is operable to both push articulation band (270) distally and pull articulation band (270) proximally, depending on which direction knob (228) is rotated, via first rivet member (291). Other suitable relationships will be apparent to those of ordinary skill in the art in view of the teachings herein. It should also be understood that drive member (272) and/or first rivet member (291) may be rotatable relative to first lead screw (283), which may permit rotation of shaft (230) by knob (234) as described below.

As noted above, second rivet member (292) is engaged with second lead screw (284). Second rivet member (292) is disposed in a notch (264) of drive member (262). The engagement between second rivet member (292) and drive member (262) is such that second rivet member (292) and drive member (262) will translate together. In other words, second rivet member (292) both pulls drive member (262) proximally and pushes drive member (262) distally, depending on the direction in which knob (228) is rotated. Thus, second lead screw (284) is operable to both push articulation band (260) distally and pull articulation band (260) proximally, depending on which direction knob (228) is rotated. As noted above, the opposing orientations of threading (285, 286) provide simultaneous opposing translation of rivet members (291, 292) (and simultaneous opposing translation of lead screws (283, 284)), thereby providing simultaneous opposing translation of drive members (262, 272). While rivet member (291) pushes distally on the distal end of the notch in drive member (272), rivet member (292) pushes proximally on the proximal end of the notch in drive member (262). Likewise, while rivet member (292) pushes distally on the distal end of the notch in drive member (262), rivet member pushes proximally on the proximal end of the notch in drive member (272). Other suitable relationships will be apparent to those of ordinary skill in the art in view of the teachings herein. It should also be understood that drive member (262) and/or second rivet member (292) may be rotatable relative to second lead screw (284), which may permit rotation of shaft (230) by knob (234) as described below.

As noted above, articulation knob (228) is formed by a first knob half (228a) and a second knob half (228b). In some instances, forces exerted back on knob halves (228a, 228b) by lead screws (283, 284) may tend to urge knob halves (228a, 228b) to separate from each other, particularly when knob (228) is being rotated to articulate the articulation section of shaft (230) and tissue and/or friction are/is providing significant resistance to such articulation. To address these stresses on knob halves (228a, 228b), a pair of containment rings (300, 310) are positioned at each end of assembled knob (228). Containment rings (300, 310) are configured to substantially prevent knob halves (228a, 228b) from separating from each other.

Containment ring (300) includes a flange (302) and a cylindraceous portion (304). As best seen in FIG. 23, cylindraceous portion (304) include a series of notches (306) angularly arrayed about the circumference of cylindraceous portion (304). Cylindraceous portion (304) is configured to encompass complementary cylindraceous portions (320a, 320b) formed by knob halves (228a, 228b). Cylindraceous portions (320a, 320b) include axially extending protrusions (322a, 322b) that are received in notches (306) of cylindraceous portion (304) when knob (228) is assembled with containment ring (300). This engagement provides unitary rotation of containment ring (300) with knob halves (228a, 228b).

As best seen in FIGS. 19-20, flange (302) of containment ring (300) engages bosses (227) of housing (221). Bosses (227) restrain containment ring (300) in the radial and axial directions, but permit rotation of containment ring (300) relative to housing (221). In some versions, flange (302) and/or the entire containment ring (300) comprises a low friction material to minimize frictional resistance due to contact between flange (302) and bosses (227). For instance, flange (302) may be formed of a low friction material or may be coated with a low friction material. In addition or in the alternative, bosses (227) may comprise a low friction material. In either case, flange (302) and bosses (227) may provide a relatively low friction bearing surface as an interface between knob (228) and housing (221). Various suitable materials that may be used for flange (302), the entire containment ring (300), and/or bosses (227) will be apparent to those of ordinary skill in the art in view of the teachings herein.

Figure 24:
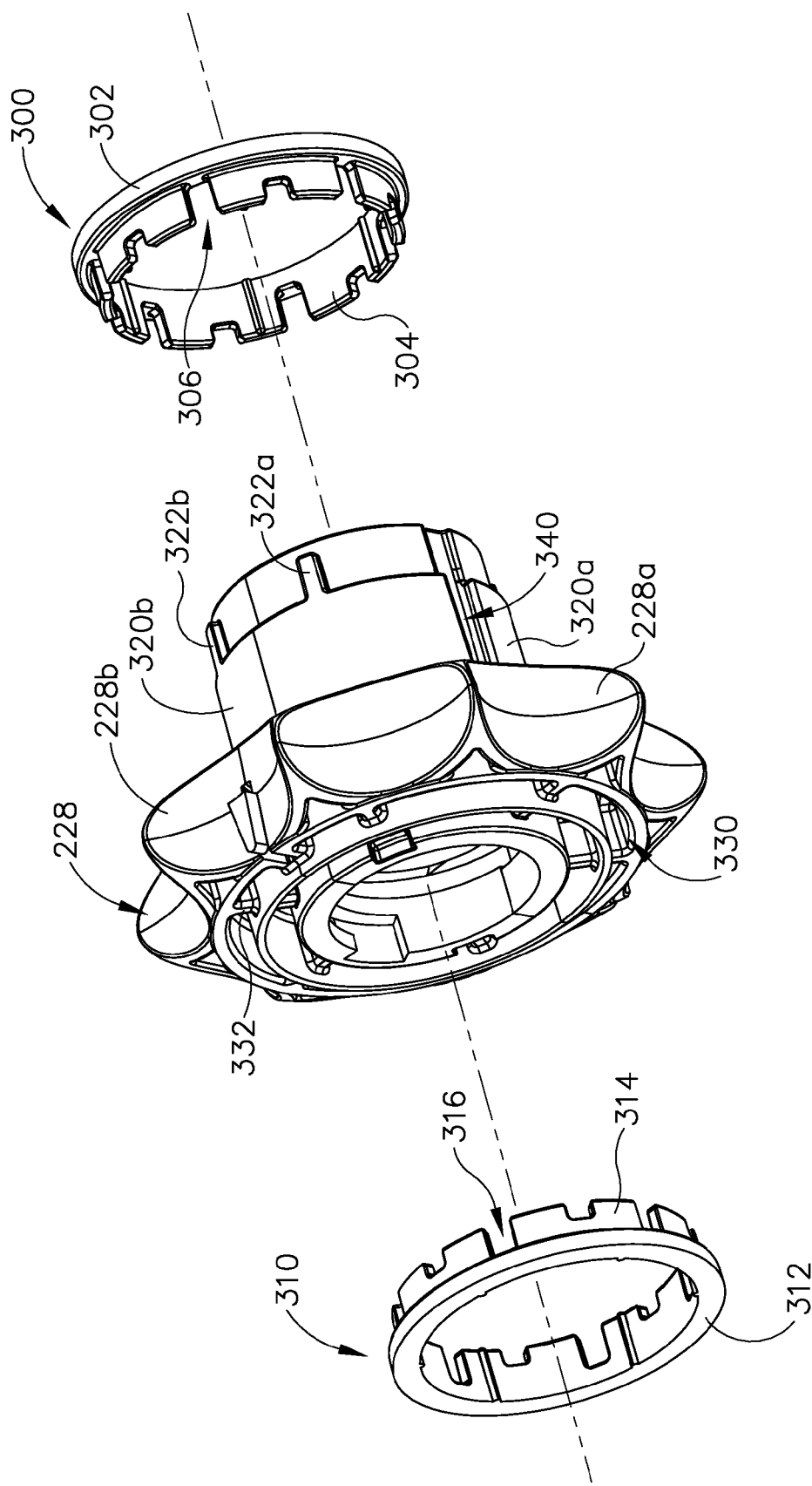
FIG. 24 depicts another exploded perspective view of some of the articulation control components of the handle assembly of FIG. 18.

Containment ring (310) is configured similar to containment ring (300). In particular, containment ring (310) includes a flange (312) and a cylindraceous portion (314). As best seen in FIG. 23, cylindraceous portion (314) include a series of notches (316) angularly arrayed about the circumference of cylindraceous portion (314). As best seen in FIGS. 23-24, assembled knob (228) defines an annular recess (330) that includes a plurality of radially extending ribs (332). Annular recess (330) is configured to receive cylindraceous portion (314) of containment ring (310), with ribs (332) being received in notches (316). This engagement provides unitary rotation of containment ring (310) with knob halves (228a, 228b).

As best seen in FIGS. 19-20, flange (312) of containment ring (310) engages bosses (229) of housing (221). Bosses (229) restrain containment ring (310) in the radial and axial directions, but permit rotation of containment ring (310) relative to housing (221). In some versions, flange (312) and/or the entire containment ring (310) comprises a low friction material to minimize frictional resistance due to contact between flange (312) and bosses (229). For instance, flange (312) may be formed of a low friction material or may be coated with a low friction material. In addition or in the alternative, bosses (229) may comprise a low friction material. In either case, flange (312) and bosses (229) may provide a relatively low friction bearing surface as an interface between knob (228) and housing (221). Various suitable materials that may be used for flange (312), the entire containment ring (310), and/or bosses (229) will be apparent to those of ordinary skill in the art in view of the teachings herein.

While knob (228) is formed of two halves (228a, 228b) in the present example, it should be understood that any suitable number of pieces may be used to form knob, including just one piece or three or more pieces. In versions where three or more pieces are held together, containment rings (300, 310) may substantially hold such pieces together in accordance with the teachings above.

In some instances, it may be desirable to provide some form of feedback to the surgeon to indicate the degree of articulation in the articulation section of shaft (230). Such feedback may be visual, audible, and/or tactile. A surgeon may wish to receive such feedback before withdrawing shaft (230) from a patient via a trocar, such as to confirm that the articulation section is in a substantially straight configuration before withdrawal. As a merely illustrative example of visual feedback, a marking may be provided on the exterior of housing (221) and/or on the exterior of knob (228). For instance, housing (221) and knob (228) may include complementary arrows that align when the articulation section of shaft (230) is in a straight configuration. As another merely illustrative example of visual feedback, the articulation section of shaft (230) may include a high-contrast line or other visual indicator that may enhance visualization of the degree of articulation of the articulation section. For instance, a high-contrast line may make it easier to see how straight or bent the articulation section is, since the line will bend or straighten in accordance with the articulation state of the articulation section. Providing a line or other marking on the articulation section may facilitate viewing of the marking within the image provided by an endoscopic camera, such that the surgeon need not look away from the surgical field presented on a screen coupled with the endoscopic camera in order to determine the degree of articulation of the articulation section. Other suitable ways of providing visual feedback to indicate articulation states will be apparent to those of ordinary skill in the art in view of the teachings herein.

Figure 25:
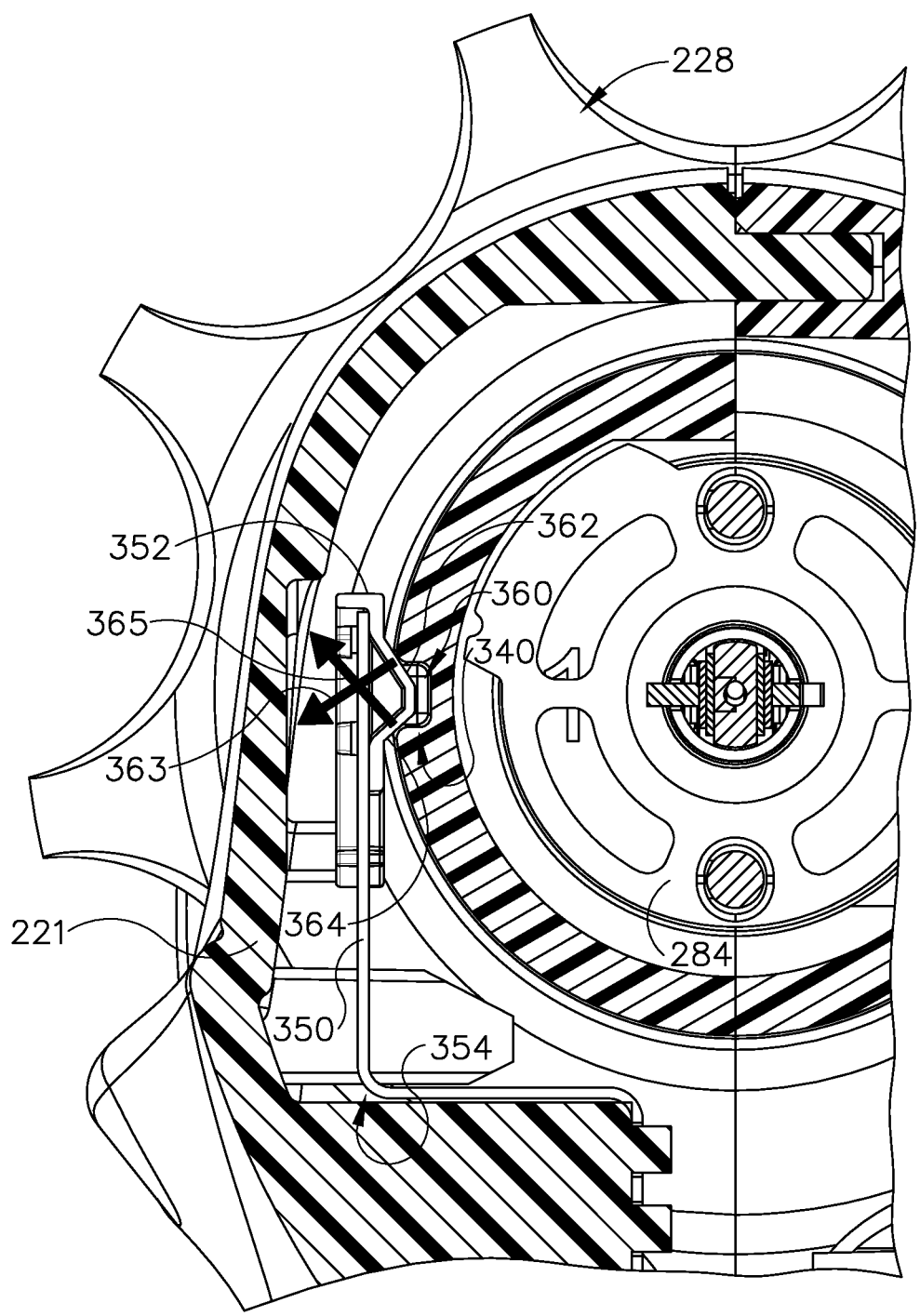
FIG. 25 depicts a cross-sectional end view of a detent feature of the articulation control components of the handle assembly of FIG. 18, taken along line 25-25 of FIG. 18.

Instrument (200) of the present example includes features for providing audible and tactile feedback relating to the articulation state of the articulation section of shaft (230). In particular, and as shown in FIGS. 18, 23, and 25, a detent arm (350) is secured to housing (221). Detent arm (350) includes a detent pad (352) that has a protrusion (360) that is configured to snap into a longitudinal recess (340) formed in cylindraceous portion (320a) of knob half (228a). In the present example, recess (340) is only provided in knob half (228a), and knob half (228b) does not include any similar recess. Detent arm (350) is resiliently biased to urge detent pad (352) radially inwardly toward knob half (228a). Recess (340) is positioned such that the protrusion of detent pad (352) will snap into recess (340) when the articulation section of shaft (230) is in a substantially straight configuration. When knob (228) is rotated to articulate the articulation section, detent arm (350) will deform and detent pad (352) will be deflected away from recess (340). In particular, detent arm (350) will effectively pivot at a bent portion (354) of detent arm (350), which is adjacent to housing (221).

As best seen in FIG. 25, protrusion (360) includes an upper angled surface (362) and a lower angled surface (364). Angled surfaces (362, 364) are configured to provide a generally smooth transition for protrusion (360) into and out of recess (340). In some versions, angled surfaces (362, 364) are substantially symmetric, such that angled surfaces (362, 364) define complementary angles with detent arm (350). In the present example, however, angled surfaces (362, 364) are asymmetric. In particular, upper surface (362) defines an angle with detent arm (350) that is greater than the angle defined between lower surface (364) and detent arm (350). In other words, upper surface (362) is at a more obtuse angle than lower surface (364).

The asymmetry of surfaces (362, 364) in the present example may provide a substantially symmetric force profile when knob (228) is initially rotated to the left (counterclockwise) or right (clockwise) from the home position (i.e., from the position where protrusion (360) is disposed in recess (340)). Conversely, in versions where surfaces (362, 364) are symmetric, the forces exerted by cylindraceous portion (320a) at recess (340) against protrusion (360) may be greater when knob (228) is initially rotated to the left (counterclockwise) than the forces exerted by cylindraceous portion (320a) at recess (340) against protrusion (360) when knob (228) is initially rotated to the right (clockwise). In other words, symmetric surfaces (362, 364) may in fact provide greater resistance to initial left (counterclockwise) rotation of knob (228) than the resistance provided to initial right (clockwise) rotation of knob (228). This may be due to the fact that forces exerted by cylindraceous portion (320a) at recess (340) against lower surface (364) are directed substantially away from the pivot provided by bent portion (354) when knob (228) is initially rotated to the right (clockwise), as indicated by arrow (365); whereas the forces exerted by cylindraceous portion (320a) at recess (340) against upper surface (362) are directed more generally toward the pivot provided by bent portion (354) when knob (228) is initially rotated to the left (counterclockwise), as indicated by arrow (363). Bent portion (354) thus itself provides increased resistance to left (counterclockwise) rotation of knob (228).

Referring back to the present example, orienting upper surface (362) at a more obtuse angle will deflect the forces against surface (362) further away from the pivot provided by bent portion (354) when knob (228) is initially rotated to the left (counterclockwise). In FIG. 25, arrow (365) shows force exerted by cylindraceous portion (320a) at recess (340) against lower surface (364) when knob (228) is initially rotated to the right (clockwise). Arrow (363) shows force exerted by cylindraceous portion (320a) at recess (340) against upper surface (362) when knob (228) is initially rotated to the left (counterclockwise). Arrow (363) is directed further away from the pivot provided by bent portion (354) than it would otherwise be if upper surface (362) were symmetric with lower surface (364). The more obtuse the angle of upper surface (362) is, the less resistance upper surface (362) will provide to left (counterclockwise) rotation of knob (228) from the home position. The angle of upper surface (362) in the present example is selected to provide a substantially equal resistance force to initial rotation of knob (228) from the home position in the left (counterclockwise) direction as the resistance force encountered with initial rotation of knob (228) from the home position in the right (clockwise) direction. Other suitable configurations for protrusion (360) will be apparent to those of ordinary skill in the art in view of the teachings herein.

It should also be understood that the symmetry/asymmetry of surfaces (362, 364) may have a negligible effect on rotation of knob (228) once knob (228) has substantially left the home position (e.g., when protrusion (360) is completely displaced from recess (340)). Detent arm (350) and detent pad (352) do not substantially interfere with the free rotation of knob (228); and that the friction between detent pad (352) and cylindraceous portions (320a, 320b) will be negligible when detent pad (352) is disengaged from recess (340). It should also be understood that when detent pad (352) snaps into engagement with recess (340) (e.g., upon straightening of the articulation section), this snapping engagement may heard by the surgeon and/or be felt by the surgeon through handpiece (220). Other suitable ways of providing audible and/or tactile feedback to indicate one or more articulation states will be apparent to those of ordinary skill in the art in view of the teachings herein.

It should be understood that the above described articulation control components of instrument (200) may operate in a manner that is substantially similar to the manner that is shown in FIGS. 17A-17C and described above. Alternatively, the above described articulation control components of instrument (200) may operate in some other fashion. It should also be understood that, as described above with respect to instrument (100), manufacturing inconsistencies may be addressed at the distal ends of bands (260, 270). For instance, before the distal ends of bands (260, 270) are secured to the proximal portion of the end effector, the articulation section may be held in a straight configuration and bands (260, 270) may be pulled distally to remove any slack in bands (260, 270). With bands (260, 270) both being in tension, bands (260, 270) may then be welded or otherwise secured to the proximal portion of the end effector. As previously noted, this form of calibration is not limited to instruments (100, 200), such that this form of calibration may be readily applied to various other instruments described herein, among others. Other suitable structures and methods for calibration will be apparent to those of ordinary skill in the art in view of the teachings herein.

IV. Exemplary Shaft Rotation Control Configurations

As noted above, instrument (10, 100) may provide rotation of an end effector (40, 140) and/or shaft (30, 130) via a knob (34, 134). Likewise, instrument (200) may provide rotation of its end effector and/or shaft (230), relative to handpiece (220), via a knob (234). Such rotation may provide rotation of the end effector and shaft (230) unitarily. In some other versions, knob (234) is operable to rotate end effector (240) without rotating any portion of shaft (230) that is proximal of the articulation section. As another merely illustrative example, electrosurgical instrument (200) may include one rotation control that provides rotatability of shaft (230) and the end effector as a single unit; and another rotation control that provides rotatability of the end effector without rotating any portion of shaft (230) that is proximal of the articulation section. Other suitable rotation schemes will be apparent to those of ordinary skill in the art in view of the teachings herein.

In some instances, it may be desirable to selectively lock the rotational position of shaft (30, 130, 230) and/or the end effector (40, 140). By way of example only, instrument (10, 100, 200) may include a pivoting member, sliding member, or some other type of manually movable member that selectively engages a feature that is integral with knob (34, 134, 234) and thereby positively secures the rotational position of knob (34, 134, 234) relative to handpiece (20, 120, 220). Such a rotational locking feature may be controlled manually from handpiece (20, 120, 220) at any time during use of instrument (10, 100, 200). Various suitable forms that such a manual rotational locking feature may take will be apparent to those of ordinary skill in the art in view of the teachings herein.

As another merely illustrative variation, instrument (10, 100, 200) may be configured to selectively lock the rotational position of shaft (30, 130, 230) and/or end effector (40, 140) whenever the articulation section (36, 136) is in an articulated configuration. In other words, such versions of instrument (10, 100, 200) may be configured to permit rotation of shaft (30, 130, 230) and/or end effector (40, 140) only when the articulation section (36, 136) is in a straight configuration. This selective locking of rotation may be automatically based on the articulation state of the articulation section (36, 136), such that the user need not provide a separate rotation lock input.

Figure 28:
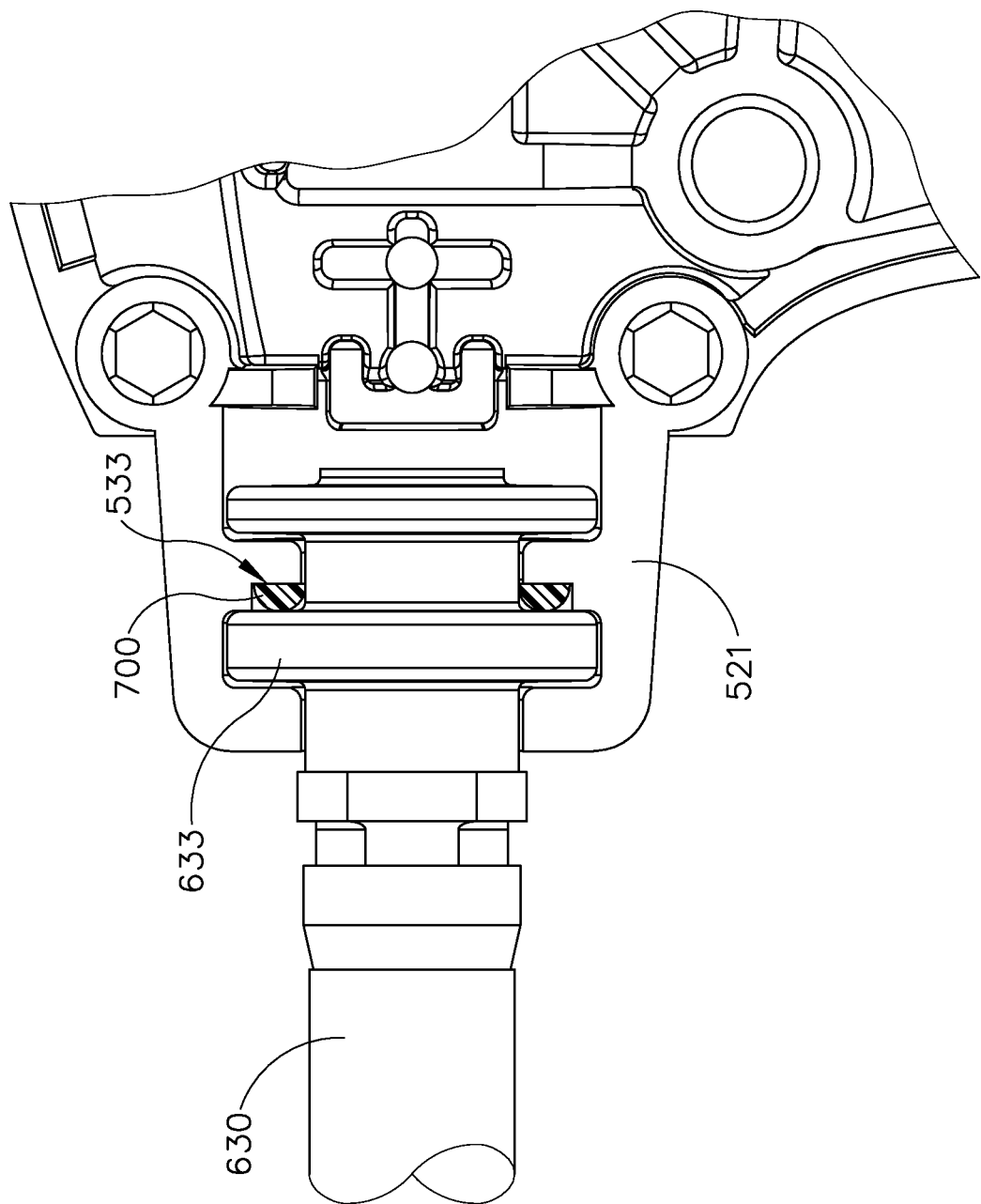
FIG. 28 depicts a partial side view distal portion of an exemplary alternative handle assembly, with a housing half and other components removed to reveal an exemplary friction ring.

FIGS. 26-28 show an example of features that may be used to provide automatic locking of rotation of shaft (30, 130, 230) and/or the end effector (40, 140) when the articulation section (36, 136) is in a bent configuration. These features nevertheless permit rotation of shaft (30, 130, 230) and/or the end effector (40, 140) when the articulation section (36, 136) is in a straight configuration. In particular, FIG. 26 shows an exemplary alternative rivet member (491). This rivet member (491) includes a series of distally extending protrusions (495) angularly arrayed on the distal face (493) of rivet member (491). Protrusions (495) are spaced such that a plurality of gaps (497) are positioned between protrusions (495). FIG. 27 shows rivet member (491) positioned in first lead screw (283), though it should be understood that first lead screw (183) may also be fitted with a feature similar to rivet member (491). FIG. 27 also shows second lead screw (284) fitted with a second rivet member (492), which is substantially identical to first rivet member (491). In this example, drive member (272) includes a distal lateral protrusion (273) that is spaced distally from rivet member (491) when the articulation section is in a straight configuration. Similarly, a distal lateral protrusion (263) of drive member (262) is spaced distally from rivet member (492). This spacing permits shaft (230), the end effector, and rotationally linked components including drive members (272, 273) to rotate relative to rivet members (491, 492) and relative to housing (221) when knob (234) is rotated.

When knob (228) is rotated in a first rotational direction bend the articulation section in a first direction, first lead screw (283) advances distally while second lead screw (284) moves proximally. The distal movement of first lead screw (283) results in entry of lateral protrusion (273) into one of the gaps (497) of rivet member (491). With lateral protrusion (273) so positioned, protrusions (495) of rivet member (491) substantially secure the rotational position of lateral protrusion (273). Since the rotational positions of rivet member (491) and first lead screw (283) are fixed relative to housing (221) via pins (223), and since the rotational position of drive member (272) is fixed relative to shaft (230) and the end effector, the positioning of lateral protrusion (273) between protrusions (495) will secure the rotational position of shaft (230) and the end effector relative to housing (221). Rivet member (491) thus prevents rotation of shaft (230) and/or the end effector when the articulation section is bent in a first direction. When the articulation section is later straightened by rotating knob (228) in a second rotational direction, lateral protrusion (273) eventually exits gap (497) and is spaced away from rivet member (491), such that rivet member (491) no longer prevents shaft (230) and/or the end effector from rotating relative to housing (221).

Similarly, when knob (228) is rotated in a second direction to bend the articulation section in a second direction, second lead screw (284) advances distally while first lead screw (283) moves proximally. The distal movement of second lead screw (284) results in engagement between second rivet member (492) and lateral protrusion (263) in a manner similar to that described above for first rivet member (491) and lateral protrusion (273). Rivet member (492) thus prevents rotation of shaft (230) and/or the end effector when the articulation section is bent in a second direction. When the articulation section is later straightened by rotating knob (228) in the first rotational direction, lateral protrusion (263) eventually disengages rivet member (492), such that rivet member (492) no longer prevents shaft (230) and/or the end effector from rotating relative to housing (221). In some versions, rivet members (491, 492) include angularly arrayed recesses in place of protrusions (495), such that rivet members (491, 492) lock rotation of shaft (230) and/or the end effector when a corresponding lateral protrusion (273, 263) is disposed in one of the recesses. In some such versions, lateral protrusions (263, 273) include proximally extending portions to enter the recesses of rivet members (491, 492). Other suitable ways in which rotation of shaft (30, 130, 230) and/or end effector (40, 140) may be automatically locked based on the articulation state of the articulation section (36, 136) will be apparent to those of ordinary skill in the art in view of the teachings herein.

As yet another merely illustrative variation, instrument (10, 100, 200) may be configured to provide relatively low resistance to rotation of shaft (30, 130, 230) and/or end effector (40, 140) when the articulation section (36, 136) is in a straight configuration; yet provide relatively high resistance to rotation of shaft (30, 130, 230) and/or end effector (40, 140) when the articulation section (36, 136) is in an articulated configuration. Some such versions may still permit rotation of shaft (30, 130, 230) and/or end effector (40, 140) when the articulation section (36, 136) is in an articulated configuration, albeit at a higher resistance than that encountered when the articulation section (36, 136) is in a straight configuration. FIG. 28 shows one merely illustrative example of a feature that may be used to provide varied resistance to rotation of shaft (30, 130, 230) and/or end effector (40, 140). In particular, FIG. 28 shows a friction ring (700) positioned in a recess (533) of housing (521). Friction ring (700) is positioned to contact a flange (633) that is unitary with shaft (630). It should be understood that housing (521) may be viewed as being otherwise analogous to housing (121, 221); and shaft (630) analogous to shaft (130, 230), etc.

Friction ring (700) may comprise any suitable material, including but not limited to rubber, silicone, isoprene, some other type of elastomeric material, etc. In the present example, friction ring (700) is compressed between flange (633) and housing (521) by approximately 0.005 inches when the articulation section of shaft (630) is in a substantially straight configuration. This may provide some relatively low resistance to rotation of shaft (630) relative to housing (521). When the articulation section of shaft is bent to an articulated configuration (e.g., using one of the articulation assemblies described above, etc.), this may produce backloading on shaft (630), such that shaft (630) is urged proximally even by a slight degree. This may further compress friction ring (700), which may in turn increase the friction between friction ring (700) and flange (633). This increased friction may thereby provide additional resistance to rotation of shaft (630) when the articulation section is bent to an articulated configuration.

Figure 29:
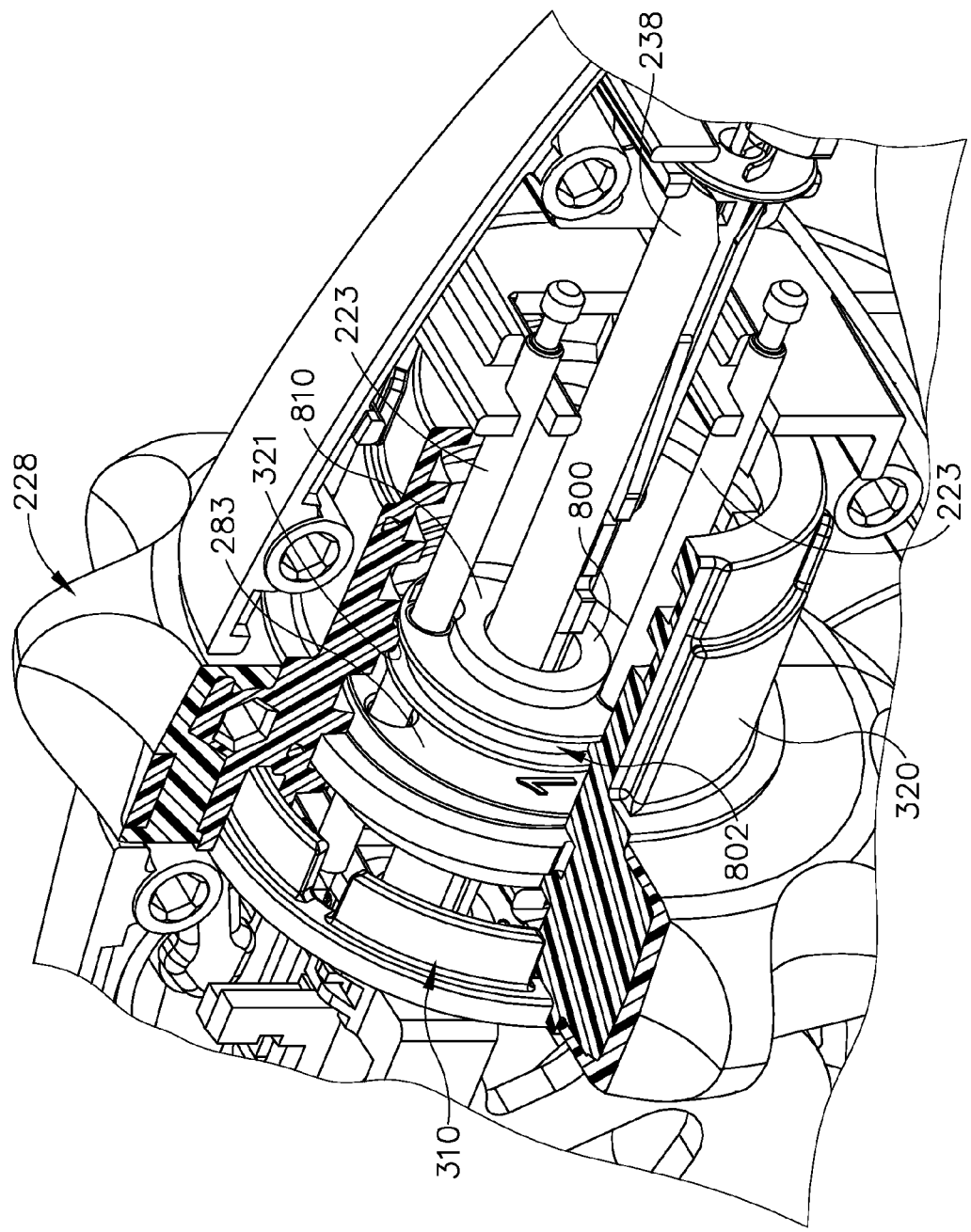
FIG. 29 depicts a partial perspective view of exemplary articulation braking features that may be used in the articulation control components of a handle assembly.
Figure 30A:
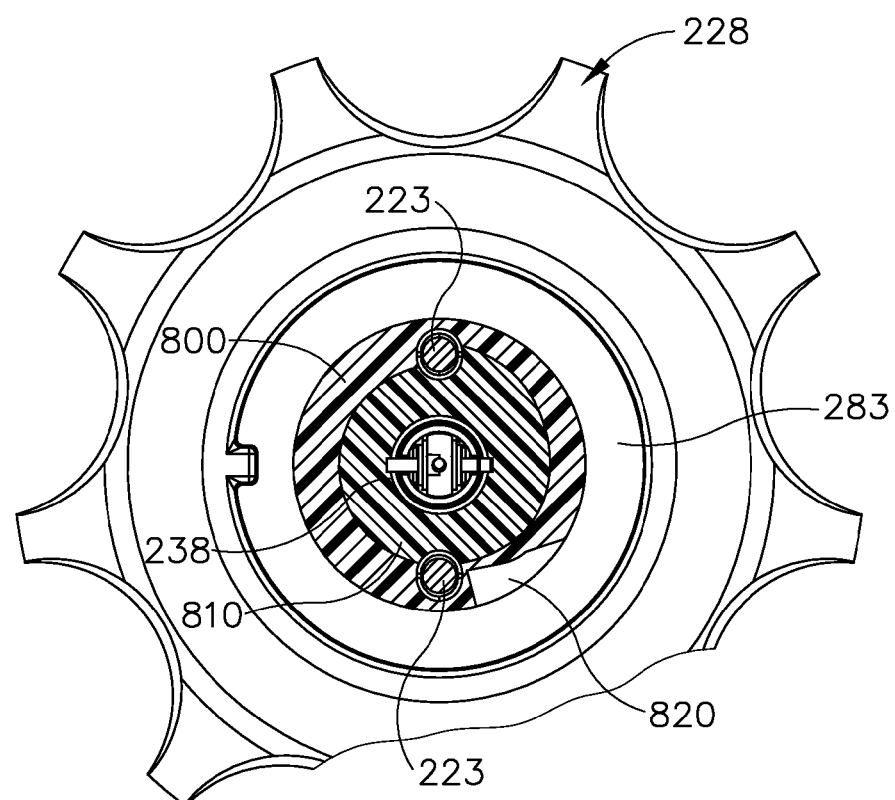
FIG. 30A depicts an end view of the articulation braking features of FIG. 29, with the knob at a home position where the articulation section of the shaft is substantially straight.
Figure 30B:
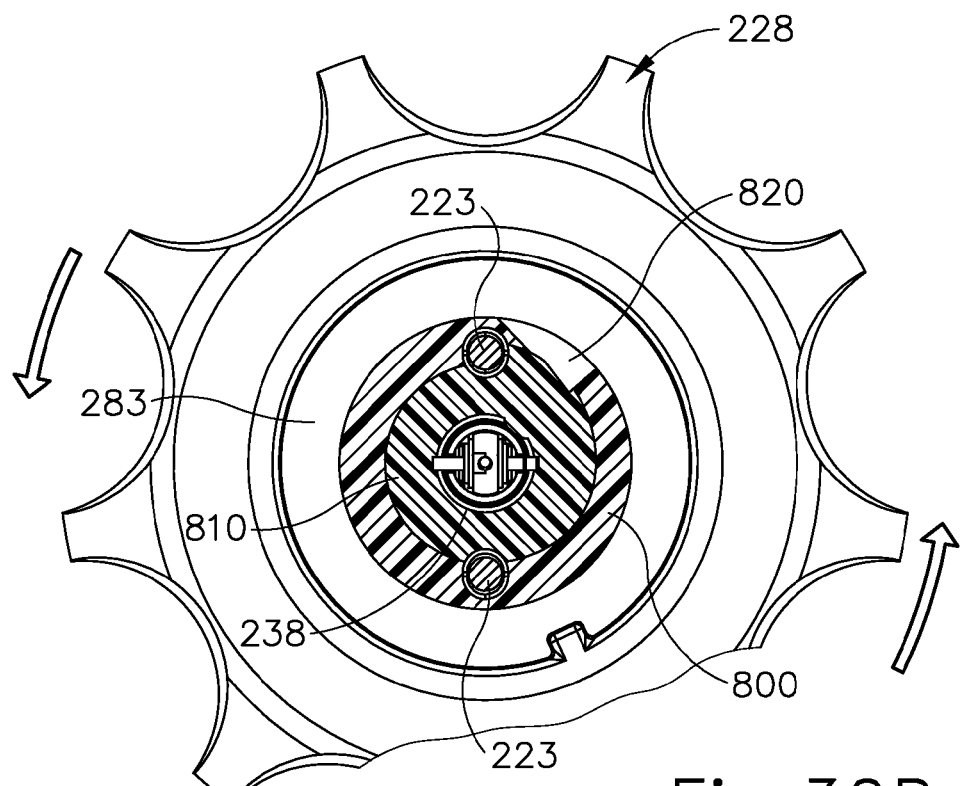
FIG. 30B depicts an end view of the articulation braking features of FIG. 29, with the knob at a rotated position where the articulation section of the shaft is substantially articulated.

FIGS. 29-30B show yet another merely illustrative example of features that may be used to provide varied resistance to rotation of shaft (30, 130, 230) and/or end effector (40, 140). In particular, FIG. 29 shows a brake disc (800) that includes an integral elastomeric brake pad (810). In the present example, disc (800) is positioned between lead screws (283, 284), though it should be understood that disc (800) may alternatively be positioned distal to lead screw (283) or proximal to lead screw (284). It should also be understood that lead screw (284) is omitted from FIG. 29 for clarity. Cylindraceous portion (320) of knob (228) Includes an inwardly extending annular flange (321), which is received in an annular recess (802) formed in the outer perimeter of disc (800). This relationship between flange (321) and recess (802) longitudinally restrains disc (800) within cylindraceous portion (320) while still permitting knob (228) to rotate relative to disc (800). Pins (223) pass through disc (800) and prevent disc (800) from rotating.

As best seen in FIGS. 30A-30B, pad (810) has a non-circular profile, with an outer profile resembling that of a nautilus shell. As also seen in FIGS. 30A-30B, cylindraceous portion (320) includes in inwardly extending cam fin (820) that progressively engages the outer perimeter of pad (810) when knob (228) (and, hence, cylindraceous portion (320)) is rotated. In particular, FIG. 30A shows the components positioned when knob (228) is at the home position, with the articulation section of shaft (230) in a substantially straight configuration. At this stage, cam fin (820) is spaced away from pad (810). FIG. 30B shows the components positioned when knob (228) (and, hence, cylindraceous portion (320)) has been rotated to the left (counterclockwise) to bend the articulation section in a first direction. At this stage, cam fin (820) bears into pad (810). It should be understood that cam fin (820) will begin bearing into pad (810) during part of the transition from the stage shown in FIG. 30A to the stage shown in FIG. 30B, and the degree of this bearing into pad (810) by cam fin (820) will progressively increase as knob (228) continues to rotate. As can also be seen in FIG. 30B, the bearing of cam fin (820) into the outer perimeter of pad (810) causes pad (810) to deform and thereby cause the inner diameter of pad (810) to bear against cutting member driver tube (238). This bearing of pad (810) against cutting member driver tube (238) provides frictional resistance against rotation of cutting member driver tube (238), and hence, against rotation of shaft (230). Thus, rotation of knob (228) to articulate the articulation section of shaft (230) will substantially prevent rotation of shaft (230) relative to handpiece (220). Furthermore, the resistance to rotation of shaft (230) relative to handpiece (220) will increase in proportion to the articulation angle defined by the articulation section of shaft (230).

While the example shown in FIGS. 29-30B and described above provides increasing resistance to rotation of shaft (230) relative to handpiece (220) in response to left (counterclockwise) rotation of knob (228), it should be understood that similar components may be used to provide increasing resistance to rotation of shaft (230) relative to handpiece (220) in response to right (clockwise) rotation of knob (228). For instance, such components may include a brake pad and cam fin that are essentially a mirror image of pad (810) and fin (820) shown in FIGS. 29-30B. In some versions, pad (810) is provided on the proximal face of disc (800) while a mirror image of pad (810) is provided on the distal face of disc (800). In some other versions, a mirror image of pad (810) is provided on a separate disc. Other suitable ways in which rotation of shaft (30, 130, 230) and/or end effector (40, 140) may be selectively resisted based on the articulation state of the articulation section (36, 136) will be apparent to those of ordinary skill in the art in view of the teachings herein.

In versions of instrument (10, 100, 200) that provide rotation of a shaft (30, 130, 230) and/or the end effector (40, 140), instrument (10, 100, 200) may provide some form of user feedback relating to the rotational position of shaft (230) and/or the end effector. For instance, rotation knob (34, 134, 234) and/or shaft (30, 130, 230) and/or the end effector (40, 140) may include one or more markings facilitating visual identification of the rotational position. A user may correlate a marking on a rotation knob (34, 134, 234) with a corresponding marking on shaft (30, 130, 230) and/or the end effector (40, 140) to better understand the orientation of such components with respect to the patient and instrument (10, 100, 200). Providing a marking on the articulation section (36, 136), on the end effector (40, 140), and/or on some other portion of instrument (10, 100, 200) that will be positioned within the patient may facilitate viewing of the marking within the image provided by an endoscopic camera, such that the surgeon need not look away from the surgical field presented on a screen coupled with the endoscopic camera in order to determine the rotational orientation of the end effector. In addition to or as an alternative to visual markings, instrument (10, 100, 200) may include a detent feature and/or some other feature(s) that are operable to provide audible and/or tactile feedback to indicate rotational orientation of the end effector. Various other suitable ways in which rotation of the end effector and associated feedback may be provided will be apparent to those of ordinary skill in the art in view of the teachings herein. Of course, some versions of instrument (10, 100, 200) may lack rotatability of the end effector.

V. Miscellaneous

It should be understood that any of the versions of electrosurgical instrument (10) described herein may include various other features in addition to or in lieu of those described above. By way of example only, any of the devices herein may also include one or more of the various features disclosed in U.S. Pub. No. 2012/0078243, entitled "Control Features for Articulating Surgical Device," published Mar. 29, 2012, the disclosure of which is incorporated by reference herein; U.S. Pub. No. 2012/0078244, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, now U.S. Pat. No. 9,402,682, the disclosure of which is incorporated by reference herein; U.S. Pub. No. 2012/0078248, entitled "Articulation Joint Features for Articulating Surgical Device," published Mar. 29, 2012, now U.S. Pat. No. 9,220,559, the disclosure of which is incorporated by reference herein; and/or U.S. patent application Ser. No. 13/622,729, entitled "Surgical Instrument with Multi-Phase Trigger Bias," filed Sep. 19, 2012, now U.S. Pat. No. 9,089,327, issued Jul. 28, 2015, the disclosure of which is incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that the teachings herein may be readily applied to a variety of other types of medical instruments. By way of example only, the teachings herein may be readily applied to tissue graspers, tissue retrieval pouch deploying instruments, surgical staplers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus, comprising:
(a) an end effector;
(b) an elongate shaft, wherein the elongate shaft defines a longitudinal axis, wherein the elongate shaft comprises:
(i) a distal end, wherein the end effector is positioned at the distal end of the elongate shaft,
(ii) a proximal end,

(iii) an articulation section, wherein the articulation section is operable to deflect at least part of the end effector away from the longitudinal axis,
(iv) a first lead screw, wherein the first lead screw is operable to translate longitudinally, and
(v) a second lead screw, wherein the second lead screw is operable to translate longitudinally,
wherein the first lead screw and the second lead screw are configured to translate longitudinally in opposing directions to thereby drive articulation of the end effector at the articulation section; and
(c) a handle assembly associated with the proximal end of the elongate shaft, wherein the handle assembly comprises:
(i) a rotary member, wherein the rotary member is operable to rotate about an axis of rotation to thereby cause simultaneous translation of the first lead screw and the second lead screw relative to the handle assembly shaft in opposing longitudinal directions, wherein the axis of rotation is parallel to the longitudinal axis of the elongate shaft.

2. The apparatus of claim 1, wherein the handle assembly further comprises a first lead screw member, wherein the rotary member defines internal threading engaged with the first lead screw member such that the rotary member is operable to translate the first lead screw member upon rotation of the rotary member about the axis of rotation, wherein the first lead screw member is operable to drive articulation of the end effector.

3. The apparatus of claim 2, wherein the handle assembly further comprises a second lead screw member, wherein the second lead screw member is engaged with the internal threading of the rotary member such that the rotary member is operable to translate the second lead screw member upon rotation of the rotary member about the axis of rotation, wherein the second lead screw member is operable to drive articulation of the end effector.

4. The apparatus of claim 3, wherein the threading of the rotary member includes a first thread region and a second thread region, wherein the first thread region and the second thread region have opposing pitch relative to each other.

5. The apparatus of claim 4, wherein the first lead screw member is engaged with the first thread region, wherein the second lead screw member is engaged with the second thread region.

6. The apparatus of claim 5, wherein the rotary member is operable to simultaneously translate the first lead screw member distally and translate the second lead screw member proximally in response to rotation of the rotary member in a first direction about the axis of rotation;
wherein the rotary member is further operable to simultaneously translate the first lead screw member proximally and translate the second lead screw member distally in response to rotation of the rotary member in a second direction about the axis of rotation.

7. The apparatus of claim 1, wherein the rotary member comprises at least two parts coupled together about the axis of rotation, the handle assembly further comprising one or more containment rings secured to the rotary member, wherein the one or more containment rings are operable to secure the at least two parts of the rotary member together.

8. The apparatus of claim 7, wherein the handle assembly further comprises a housing, wherein the one or more containment rings include a bearing surface engaged with the housing of the handle assembly, wherein the one or more containment rings are rotatable with the rotary member relative to the housing.

9. The apparatus of claim 7, wherein the rotary member comprises a distal end and a proximal end, wherein the one or more containment rings comprise a first containment ring and a second containment ring, wherein the first containment ring is secured to the distal end of the rotary member, wherein the second containment ring is secured to the proximal end of the rotary member.

10. The apparatus of claim 1, wherein the handle assembly further comprises a housing, wherein the rotary member further comprises a detent feature, wherein the detent feature of the rotary member is configured to engage a complementary detent feature of the housing in response to the articulation section arriving at a substantially straight configuration.

11. The apparatus of claim 1, wherein one or both of the shaft or the end effector is rotatable relative to the handle assembly.

12. The apparatus of claim 11, further comprising a rotation locking feature, wherein the rotation locking feature is configured to selectively permit or prevent rotation of the shaft or end effector relative to the handle assembly.

13. The apparatus of claim 12, wherein the rotation locking feature is configured to permit rotation of the shaft or end effector relative to the handle assembly in response to the articulation section being in a substantially straight configuration, wherein the rotation locking feature is configured to prevent rotation of the shaft or end effector relative to the handle assembly in response to the articulation section being in an articulated configuration.

14. The apparatus of claim 12, wherein the handle assembly further comprises a first member and a second member, wherein the first member is configured to translate in response to rotation of the rotary member to drive the second member longitudinally, to thereby drive articulation of the end effector;
wherein the second member is configured to rotate with the shaft or end effector;
wherein the first member is configured to selectively lock the rotational position of the second member, and thereby lock the rotational position of the shaft or end effector, in response to the first member being driven into engagement with the second member by rotation of the rotary member.

15. The apparatus of claim 11, further comprising a rotation resistance feature, wherein the rotation resistance feature is configured to provide varied resistance to rotation of the shaft or end effector relative to the handle assembly based on an articulation state of the articulation section.

16. The apparatus of claim 15, wherein the rotation resistance feature is configured to provide a first degree of resistance in response to the articulation section being substantially straight, wherein the rotation resistance feature is configured to provide a second degree of resistance in response to the articulation section being articulated, wherein the second degree of resistance is higher than the first degree of resistance.

17. The apparatus of claim 15, wherein the rotation resistance feature comprises an elastomeric material configured to provide varied frictional resistance to rotation the shaft or end effector.

18. The apparatus of claim 1, wherein the end effector comprises:
(i) a first jaw, and
(ii) a second jaw,
wherein the first jaw is movable toward the second jaw to clamp tissue between the first and second jaw, wherein at least one of the jaws comprises at least one electrode, wherein the at least one electrode is operable to deliver RF energy to tissue clamped between the first and second jaw.

19. An apparatus, comprising:
   (a) an end effector;
   (b) an elongate shaft, wherein the elongate shaft defines a longitudinal axis, wherein the elongate shaft comprises:
      (i) a distal end, wherein the end effector is positioned at the distal end of the elongate shaft,
      (ii) a proximal end, and
      (iii) an articulation section, wherein the articulation section is operable to deflect at least part of the end effector away from the longitudinal axis; and
   (c) a handle assembly associated with the proximal end of the shaft, wherein the handle assembly comprises a rotary member and a pair of lead screws, wherein the rotary member is rotatable about an axis of rotation, wherein the axis of rotation is aligned with the longitudinal axis of the elongate shaft, wherein the rotary member is operable to rotate in a single direction to thereby cause simultaneous translation of the pair of lead screws in opposing directions toward or away from one another, wherein the pair of lead screws are operable to simultaneously translate in opposing directions toward or away from one another to thereby drive articulation of the end effector.

20. An apparatus, comprising:
   (a) an end effector;
   (b) an elongate shaft, wherein the elongate shaft defines a longitudinal axis, wherein the elongate shaft comprises:
      (i) a distal end, wherein the end effector is positioned at the distal end of the elongate shaft,
      (ii) a proximal end, and
      (iii) an articulation section, wherein the articulation section is operable to deflect at least part of the end effector away from the longitudinal axis;
   (c) a handle assembly associated with the proximal end of the shaft, wherein the handle assembly comprises:
      (i) a rotary member having opposing thread regions, and
      (ii) a pair of lead screws engaged with the opposing thread regions, such that the lead screws are operable to translate simultaneously in opposite directions in response to rotation of the rotary member in a single direction; and
   (d) a pair of articulation control features extending through the elongate shaft, wherein the articulation control features are coupled with the lead screws such that the articulation control features are configured to translate simultaneously in opposite directions in response to simultaneous translation of the pair of lead screws in opposite directions, wherein the articulation control features are further coupled with the articulation section such that the articulation control features are operable to drive articulation of the end effector based on opposing translation of the lead screws and corresponding opposing translation of the articulation control features.

* * * * *